US012758262B2

(12) United States Patent
Simón Vallés et al.

(10) Patent No.: US 12,758,262 B2
(45) Date of Patent: Oct. 13, 2026

(54) SYSTEM FOR EMBRYO TRANSFER

(71) Applicant: PREMIUM FERTILITY S.L., Paterna (ES)

(72) Inventors: Carlos Simón Vallés, Paterna (ES); Javier Santamaría Costa, Barcelona (ES); David Jiménez Moreno, Paterna (ES); Dusty Fisk, Escondido, CA (US); Rhys Freitas, Ramona, CA (US); David S. Hunt, San Diego, CA (US); Robert Jenkins, San Diego, CA (US)

(73) Assignee: PREMIUM FERTILITY S.L., Paterna (ES)

( * ) Notice: Subject to any disclaimer, the term of this patent is extended or adjusted under 35 U.S.C. 154(b) by 699 days.

(21) Appl. No.: 18/249,181

(22) PCT Filed: Oct. 15, 2021

(86) PCT No.: PCT/EP2021/078712
§ 371 (c)(1),
(2) Date: Apr. 14, 2023

(87) PCT Pub. No.: WO2022/079301
PCT Pub. Date: Apr. 21, 2022

(65) Prior Publication Data

US 2023/0389961 A1 Dec. 7, 2023

(30) Foreign Application Priority Data

Oct. 15, 2020 (EP) .................................... 20382905

(51) Int. Cl.
*A61B 17/435* (2006.01)
*A61B 1/00* (2006.01)
(Continued)

(52) U.S. Cl.
CPC ........ *A61B 17/435* (2013.01); *A61B 1/00151* (2013.01); *A61B 1/0016* (2013.01);
(Continued)

(58) Field of Classification Search
CPC . A61B 17/435; A61B 1/00151; A61B 1/0016; A61B 1/303; A61B 90/30;
(Continued)

(56) References Cited

U.S. PATENT DOCUMENTS

2004/0122286 A1 6/2004 Kamrava
2007/0112251 A1 5/2007 Nakhuda
(Continued)

FOREIGN PATENT DOCUMENTS

EP 1166720 B1 12/2008
JP 2009508642 A 3/2009
KR 10-2019-0008927 A 1/2019

*Primary Examiner* — Carrie R Dorna
*Assistant Examiner* — Joshua Daryl D Lannu
(74) *Attorney, Agent, or Firm* — Seed Intellectual Property Law Group LLP

(57) ABSTRACT

The present invention relates to dispensing instruments and methods for introducing treatment material and fluid-like material with an embryo into a uterus. More specifically, the present invention relates to apparatuses for delivering a fertilized egg or embryo into a maternal uterine endometrium in humans or any other mammalian species and associated computer programs for controlling said apparatuses.

22 Claims, 26 Drawing Sheets

(51) Int. Cl.

| | |
|---|---|
| ***A61B 1/008*** | (2006.01) |
| ***A61B 1/303*** | (2006.01) |
| ***A61B 17/00*** | (2006.01) |
| ***A61B 90/00*** | (2016.01) |
| ***A61B 90/30*** | (2016.01) |
| ***A61D 19/04*** | (2006.01) |
| ***A61M 25/01*** | (2006.01) |

(52) U.S. Cl.
CPC .............. *A61B 1/303* (2013.01); *A61B 90/30* (2016.02); *A61D 19/04* (2013.01); *A61B 2017/00323* (2013.01); *A61B 2017/00367* (2013.01); *A61B 2017/00557* (2013.01); *A61B 2090/0811* (2016.02)

(58) Field of Classification Search
CPC ........... A61B 2017/00323; A61B 2017/00367; A61B 2017/00557; A61B 2090/0811; A61B 1/008; A61B 2017/00314; A61B 17/00234; A61B 90/06; A61B 2090/061; A61D 19/04; A61M 25/0133; A61M 25/0136; A61M 25/0138; A61M 25/0147
See application file for complete search history.

(56) References Cited

U.S. PATENT DOCUMENTS

| | | | |
|---|---|---|---|
| 2008/0200752 | A1 | 8/2008 | Inaudi |
| 2014/0378756 | A1 | 12/2014 | Buster et al. |
| 2015/0313639 | A1 | 11/2015 | Pizolato |
| 2015/0335860 | A1 | 11/2015 | Klocke et al. |
| 2016/0374786 | A1 | 12/2016 | Gavaga |
| 2019/0159662 | A1* | 5/2019 | Papas ................. A61B 1/00032 |
| 2019/0261846 | A1 | 8/2019 | Oh et al. |
| 2019/0374711 | A1 | 12/2019 | Deliwala |

* cited by examiner

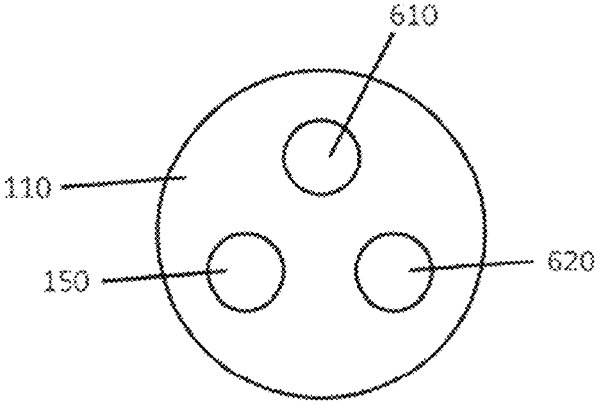
FIG 6
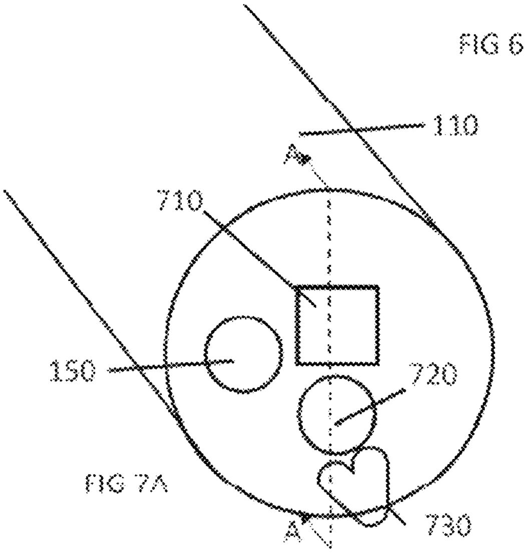
FIG 7A
FIG 7B
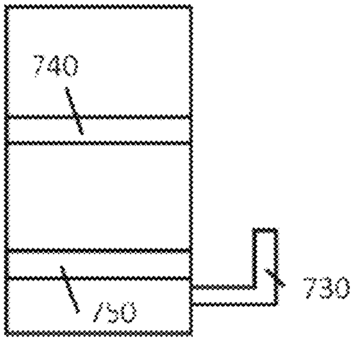
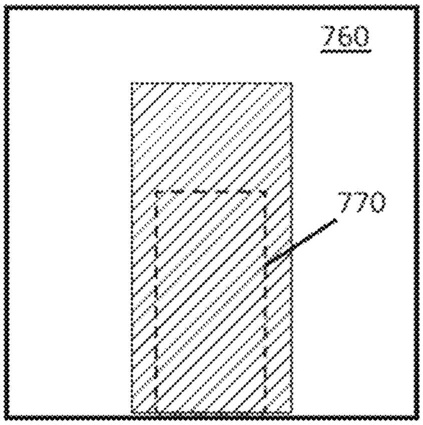
FIG 7C
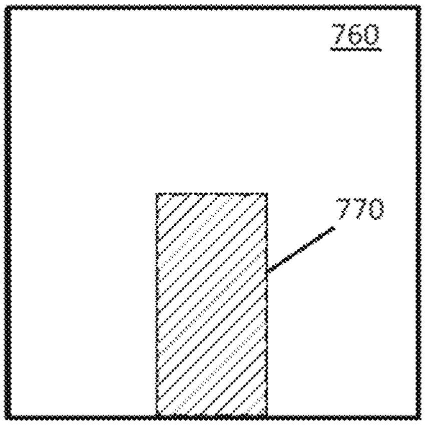
FIG 7D

SYSTEM FOR EMBRYO TRANSFER

FIELD

The present invention relates to dispensing instruments and methods for introducing treatment material and fluid-like material with an embryo into a uterus. More specifically, the present invention relates to apparatuses for delivering a fertilized egg into a uterus and associated computer programs for controlling said apparatuses.

BACKGROUND

Human In Vitro Fertilization (IVF) and Embryo Transfer (ET), first successfully performed in 1978, has become a widely practiced procedure to treat infertile couples who have failed with more conventional methods of therapy such as superovulation and intrauterine insemination. The most common indications for IVF and related procedures, such as Gamete In Vitro Fertilization or Gamete Intra-Fallopian Transfer (GIFT) which includes women having blocked or damaged fallopian tubes and includes low sperm and/or egg quality. Related factors include age of the female, and the degree of endometrial receptivity. The procedure may also be used in cases of severe male factor where direct (intra-cytoplasmic) injection of sperm is an option.

The IVF/ET procedure typically involves the hormonal stimulation of the female to first suppress her ability to ovulate on her own, then stimulate development of follicles in the ovaries with a fertility medication. The mature eggs are removed from the ovary transvaginally using a needle, preferably guided under ultrasound. Following harvesting of the eggs, the eggs are identified and sorted with regard to maturity, and then placed with a sperm sample from the male. Approximately 24 hours after fertilization, the eggs are examined to confirm fertilization, which occurs in approximately 65% to 85% of the eggs harvested.

After a short development period, the embryos are transferred, along with a volume of fluid, to the uterus using a delivery catheter. The delivery catheter is usually made of a soft plastic material to avoid damage to the endometrium. There are many potential difficulties in achieving a successful implantation. Because of the soft nature of the standard delivery catheter, in a number of cases, the tip of the catheter may bend back on itself or curve away from the fundus of the uterus. The tip may also accidentally pass between the layer of the endometrium and myometrium. Conversely, a stiffer catheter increases the risk of trauma to the uterus or cervix, with the latter possibly leading to the release of prostaglandins and expulsion of the eggs from the endometrium.

One particular difficulty in achieving successful implantation is the difficulty the surgeon has in visualizing the uterus and the endometrium into which the embryo is implanted.

SUMMARY

According to a first aspect of the invention, there is provided an apparatus suitable for delivering a fertilized egg or embryo into a maternal uterine endometrium, comprising a body configured to fit within a lumen of the female reproductive system, the body comprising: a lumen extending from a proximal end of the body to a distal portion of the body and having a distal opening at the distal portion of the body, the lumen configured to slidably receive an inner body having a distal end suitable for penetrating the endometrial epithelium; the apparatus further comprising: a first actuator operable to advance the inner body out from the distal opening of the body and a second actuator operable to expel a fertilized egg from the inner body.

In a particular embodiment, the apparatus further comprises a measurement assembly configured to measure whether the apparatus is in a first state indicating that a distance between the distal end of the inner body and the endometrial epithelium is greater than a predetermined distance, or a second state indicating that a distance between the distal end of the inner body and the endometrial epithelium is equal to or less than a predetermined distance; and an indicating device coupled to the measurement assembly and configured to indicate that the apparatus is in the first state or the second state.

In a particular embodiment, the apparatus further comprises a measurement assembly comprising a measurement portion disposed at the distal portion of the body, the measurement assembly being configured to measure whether the apparatus is in a first state indicating that a distance between the distal portion of the body and the endometrial epithelium is greater than a predetermined distance, or a second state indicating that a distance between the distal portion of the body and the endometrial epithelium is equal to or less than a predetermined distance; and an indicating device coupled to the measurement assembly and configured to indicate that the measurement assembly is in the first state or the second state;

wherein the first actuator is operable to advance the inner body out from the distal opening by at least the predetermined distance.

According to a second aspect of the invention, there is provided a computer program product configured to control the apparatus of the first aspect, wherein one or more of the actuators are electronically controlled, the computer program product comprising instructions which, when the program is executed by a computer, cause the computer to carry out the following steps: receive an instruction to actuate one or more electronically controlled actuators; and actuate the one or more electronically controlled actuators.

BRIEF DESCRIPTION OF THE DRAWINGS

To enable better understanding of the present disclosure, and to show how the same may be carried into effect, reference will now be made, by way of example only, to the accompanying schematic drawings, in which:

FIG. 6 shows a front view of a measuring portion according to one or more embodiments shown and described herein;

FIG. 7A shows a perspective view of a measuring portion according to one or more embodiments shown and described herein;

FIG. 7B shows a cross-sectional side view of the measuring portion shown in FIG. 7A taken along the line A-A;

FIGS. 7C and 7D show views of the imaging device of the measurement assembly of FIG. 7A according to one or more embodiments shown and described herein;

DETAILED DESCRIPTION

Figure 1A:
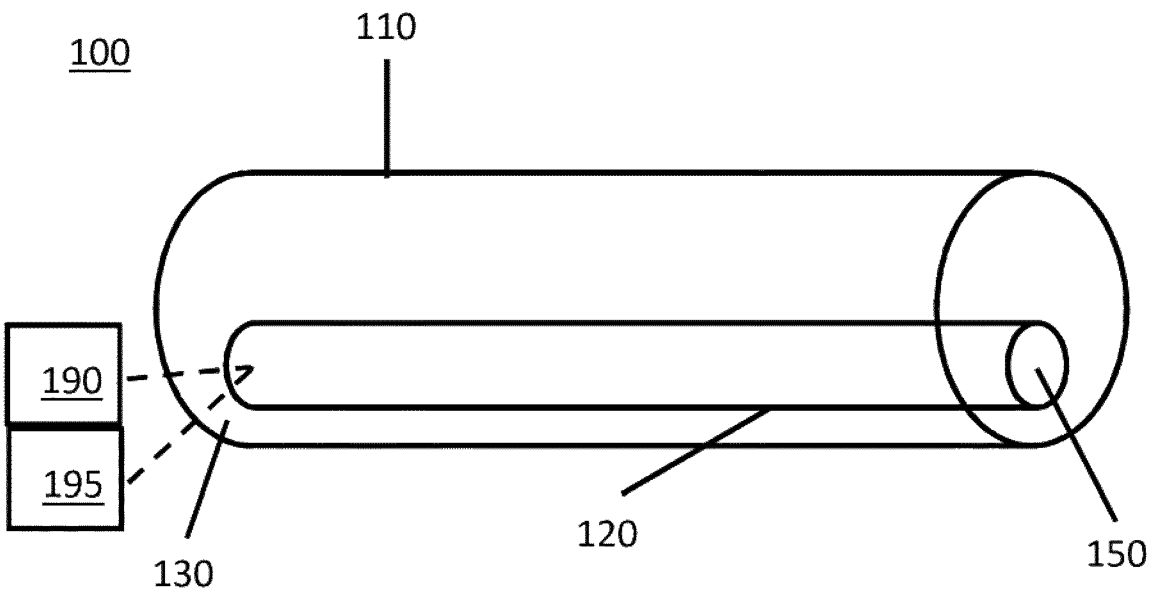
FIG. 1A shows a perspective view of an apparatus suitable for delivering a fertilized egg or embryo into a maternal uterine endometrium according to one or more embodiments shown and described herein.

FIG. 1A shows a perspective view of an apparatus 100 suitable for delivering a fertilized egg or embryo into a maternal uterine endometrium, wherein the apparatus 100 comprises a body 110 (e.g. a catheter) configured to fit within a lumen of the female reproductive system. The body comprises a lumen 120 extending from a proximal end 130 of the body 110 to a distal portion 140 of the body 110 and having a distal opening 150 at the distal portion 140 of the body. The lumen 120 is configured to slidably receive an inner body 160 having a distal end suitable for penetrating the endometrial epithelium. The apparatus 100 also comprises a first actuator 190 operable to advance the inner body 160 out from the distal opening 150 of the body 110, and a second actuator 195 operable to expel a fertilized egg or embryo from the inner body.

The dimensions of the body 110 are exaggerated in FIG. 1A-1F for the purposes of clarity, whereas in reality the body 110 is a narrow, elongate body configured to extend into the uterus to the endometrial epithelium.

Figure 1B:
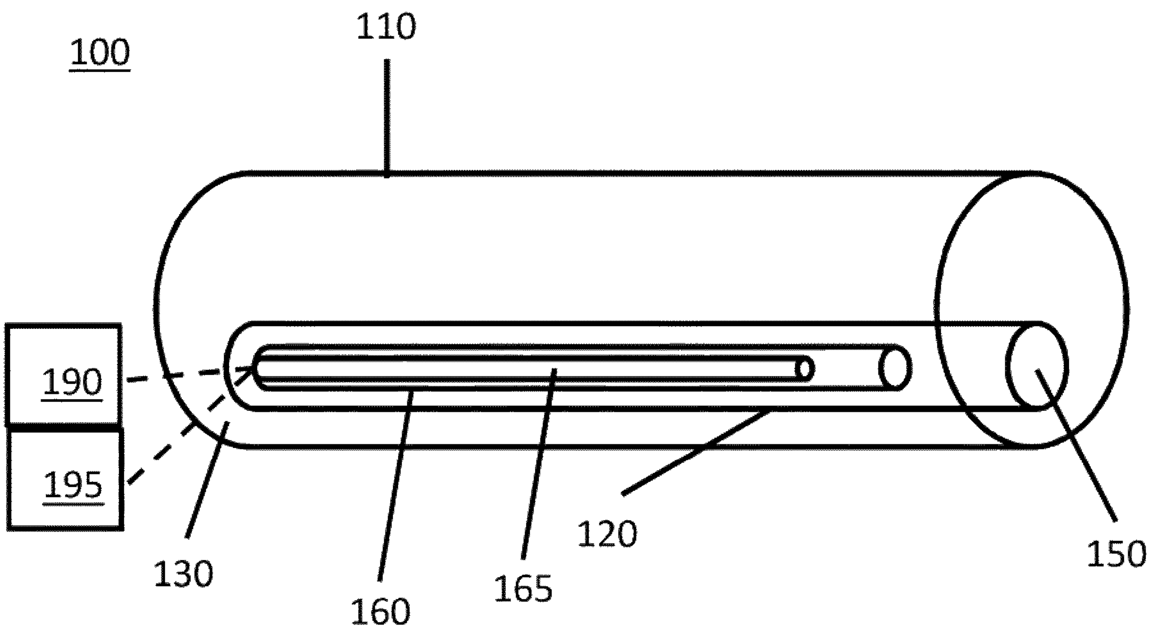
FIG. 1B shows a perspective view of another apparatus suitable for delivering a fertilized egg or embryo into a maternal uterine endometrium according to one or more embodiments shown and described herein.

FIG. 1B shows an embodiment of the apparatus 100 of FIG. 1A, wherein the apparatus 100 further includes an inner body 160 having a distal end suitable for penetrating the endometrial epithelium. In this embodiment the inner body 160 is shown located in the lumen 120 of the body 110. A plunger 165 is housed within the inner body 160 and is configured to advance towards the distal end of the inner body 160 when actuated by the second actuator 195 and expel a fertilized egg which is located inside the inner body 160.

Figure 1C:
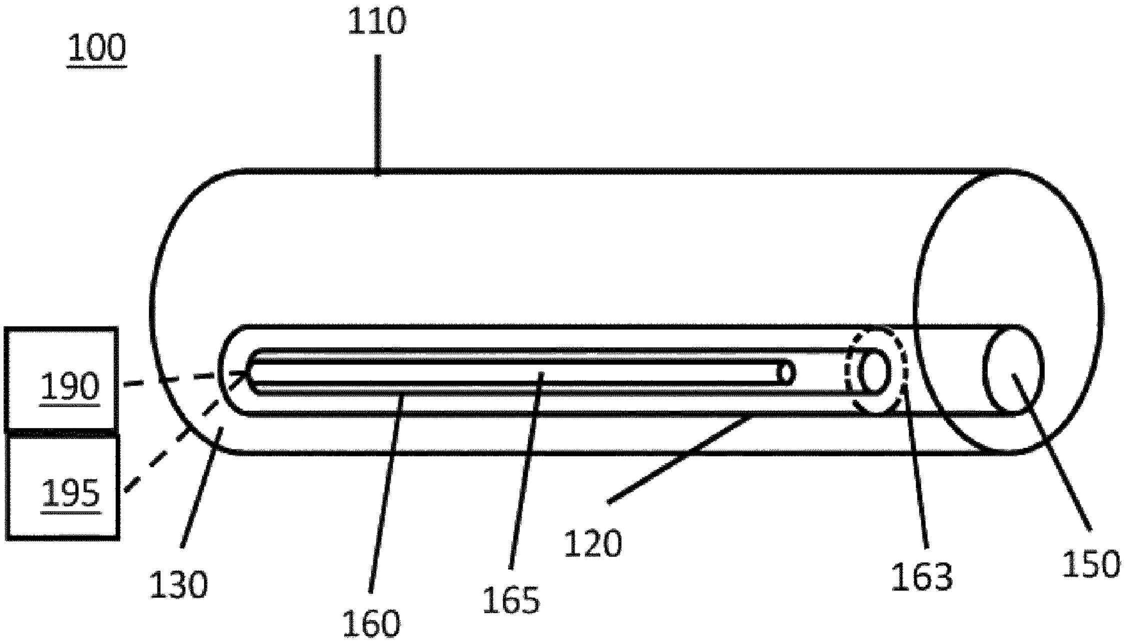
FIG. 1C shows a perspective view of another apparatus suitable for delivering a fertilized egg or embryo into a maternal uterine endometrium according to one or more embodiments shown and described herein.

FIG. 1C shows an embodiment of the apparatus 100 of FIG. 1A, wherein the apparatus further comprises a reference mark 163, present at the body 110, preferably at a distal portion of the body 110. Such reference mark 163 establishes a predetermined position of the inner body 160 within the lumen of the body 110, particularly with respect to the distal end 150 of the body 110.

As shown in FIG. 1C, the predetermined position of the distal end of the inner body 160 is located with a predefined distance offset relative to the distal end 150 of the body 110.

Figure 1D:
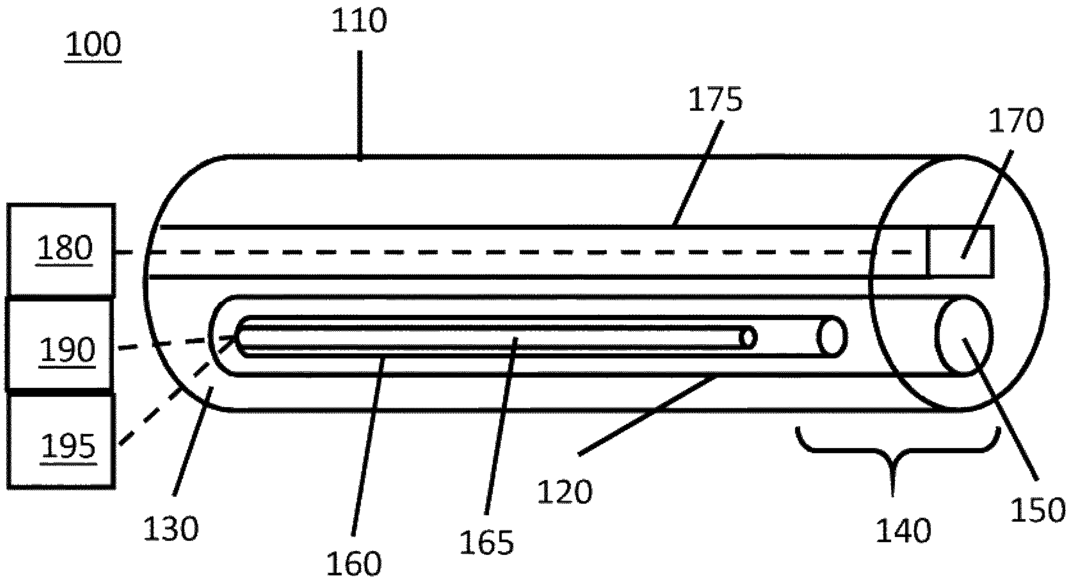
FIG. 1D shows a perspective view of another apparatus suitable for delivering a fertilized egg or embryo into a maternal uterine endometrium according to one or more embodiments shown and described herein.

FIG. 1D shows a perspective view of another apparatus 100 suitable for delivering a fertilized egg or embryo into a maternal uterine endometrium, comprising a body 110 (e.g. a catheter) configured to fit within a lumen of the female reproductive system. The body comprises a lumen 120 extending from a proximal end 130 of the body 110 to a distal portion 140 of the body 110 and having a distal opening 150 at the distal portion 140 of the body. The lumen 120 is configured to slidably receive an inner body 160 having a distal end suitable for penetrating the endometrial epithelium. The apparatus 100 further comprises a measurement assembly comprising a measurement portion 170 disposed at the distal portion 140 of the body 110 (i.e. proximal to the distal opening 150). The measurement assembly 170 is configured to measure whether the apparatus is in a first state indicating the distance between the distal opening 150 of the body 110 and the endometrial epithelium is greater than a predetermined distance (i.e. in the direction that the inner body is advanced from the distal opening 150), or a second state indicating that the distance between the distal opening 150 of the body 110 and the endometrial epithelium is equal to or less than a predetermined distance. The apparatus 100 further comprises an indicating device 180 coupled to the measurement assembly 170 and configured to indicate that the measurement assembly 170 is in the first state or the second state. The measurement assembly may be removable from the body 110. In particular, the measurement portion 170 may be slidably received in a lumen of the body such that it may be extracted from the body 110 through the lumen, meaning the measurement assembly may be reusable. The apparatus 100 also comprises a first actuator 190 operable to advance the inner body 160 out from the distal opening 150 of the body 110 by at least the predetermined distance, and a second actuator 195 operable to expel a fertilized egg from the inner body (for example to advance a plunger 165).

The predetermined distance may be, for example, less than 6 mm. The inner body may be slidable to extend from the distal opening by any suitable distance, determined by the predetermined distance to the endometrial epithelium and the desired implantation depth of the embryo. For example, the inner body 160 may be slidable to extend from 0 to 6 mm from the distal opening 150 of the body 110.

The body 110 may be an elongate body made of any suitable flexible and biocompatible material, such as PTFE, FEP, PEEK or other flexible lubricious material. Elongate body 110 and lumens may be formed, for example, by extrusion using known methods. The outer diameter of the body 110 may be between 1 mm and 1.6 mm, more preferably between 1.2 mm and 1.4 mm, and even more preferably 1.3 mm. The total length of the body 110 may be any suitable length for insertion to a position proximal to the endometrial epithelium. For example, the body 110 may have a length of 400 mm to 500 mm, for example 450 mm.

The inner body 160 may be made of any suitable biocompatible material such as PEEK and PI (Polyimide). Such materials enable the walls of the inner body 160 to be made relatively thin whilst maintaining the required rigidity of the inner body 160 for penetrating the endometrial epithelium. The inner body 160 may have any suitable outer diameter which slidably fits within the lumen 120 of the body 110. For example, the lumen 120 may have an inner diameter of greater than 0.45 mm and the outer diameter of the inner body may be about 0.45 mm.

The plunger 165 may also be made of materials such as PTFE, FEP, PEEK or other flexible lubricious material. The plunger 165 may have a suitable diameter which closely matches the inner diameter of the inner body 160 to effectively aspirate or expel fluid from the inner body 160. For example, the inner diameter of the inner body and the diameter of the plunger 165 may be about 0.28 mm.

The measurement assembly may be any suitable measurement assembly that enables it to be determined whether the distance between the distal opening 150 of the body 110 and the endometrial epithelium is greater or less than the predetermined distance. It is noted that the measurement assembly may provide a qualitative measurement (for example the measurement assembly may transition between two states) or a quantitative measurement (for example actually measuring a parameter which indicates a value of the distance to the endometrial epithelium and comparing the parameter to a threshold value indicating the predetermined distance). Both possibilities are discussed in the various embodiments disclosed herein. The measuring portion 170 is the part of the measurement assembly which is configured to interact with the endometrial epithelium in order for the measurement assembly to make the determination and may comprise any suitable element or elements. The elements of the measuring portion 170 may be connected to components at the proximal end of the apparatus 100, such as components of the measurement assembly (not shown) and the indicating device 180 via connections extending through one or more lumens 175 in the body 110. For example, the measuring portion may comprise components optically, acoustically, or electrically connected to proximal components of the measurement assembly such as light or sound emitters or receivers, electrical signal components or electrical power sources.

The indicating device 180 is coupled to the measurement assembly insofar as the difference between the two states of the measurement assembly can be determined (i.e. functionally coupled). The indicating device 180 may be any suitable device which can indicate the difference between the two states. For example, if the measurement assembly provides a qualitative visual difference between the two states, then the indicating device 180 may be a display (e.g. scope display or digital display) configured to display the visual difference to a user of the apparatus, or it may comprise suitable software and/or hardware to receive data (such as image data) from the measurement assembly and perform analysis of the data to determine the state of the measurement assembly (or display the image data). The result of the analysis may be displayed. Alternatively, the measurement assembly may comprise the software/hardware and provide the result of the analysis to the indicating device 180.

The indication provided by the indicating device 180 may be provided to a user of the apparatus 100 if the first actuator 190 is to be actuated manually by the user (for example a visual indication on a display or an audio indication from a speaker), or it may be provided as a command signal to an electronic controller (such as the motion controllers disclosed herein) if the first actuator 190 is to be actuated automatically by the electronic controller. The indication provides a means for the operator or controller to verify that the distal opening is close enough to the endometrial epithelium to deliver the fertilized egg through the inner body.

The first and second actuators 190, 195 may be any suitable actuator controllable to advance the inner body 160 and to expel the fertilized egg. For example, the first actuator 190 may be a pusher or other manual tool for advancing the inner body, or it may comprise a motor system configured to advance the inner body. Likewise, the second actuator 195 may be configured to slide a plunger movable in the inner body to pressurize fluid in the inner body distally and expel the egg. The second actuator may comprise a lead screw for advancing the plunger, i.e. the second actuator may be actuated by applying a torque, and the resulting rotary motion converted into linear motion of the plunger. The rotary actuation of the lead screw allows for a high controllability of the linear motion, and thus the aspirated and dispensed liquid volumes.

Figure 10A:
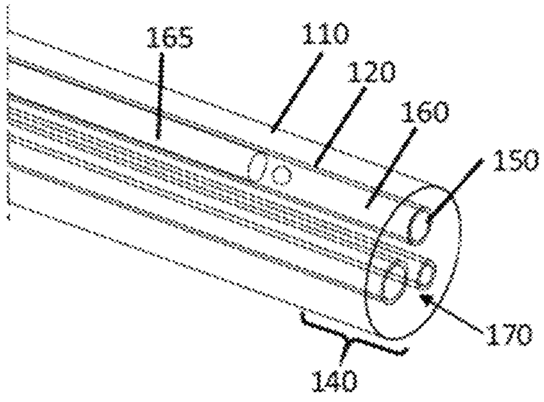
FIGS. 10A to 10D show perspective views of an apparatus according to one or more embodiments shown and described herein, in various configurations.
Figure 10B:
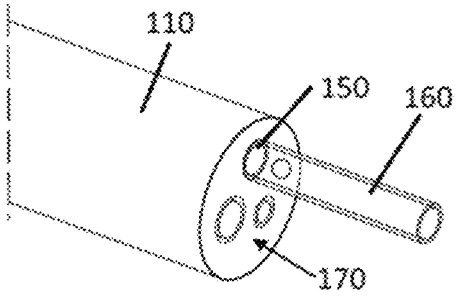
Figure 10C:
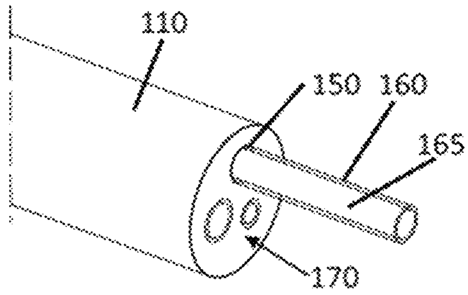
Figure 10D:
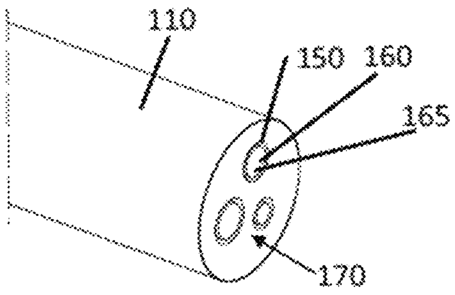

FIGS. 10A to 10D show perspective views of an apparatus wherein the second actuator is a plunger 165. When the indicating device 180 indicates that the distal opening 150 of the body 110 is at or within the predetermined distance to the endometrial epithelium, the inner body 160 may be advanced by the first actuator to penetrate the endometrial epithelium, as shown in FIG. 10B (the endometrial epithelium is not shown). Then, the second actuator 195 may advance the plunger 165 to the distal end of the inner body 160, such that the embryo is expelled, as shown in FIG. 10C. Finally, the plunger 165 and inner body 160 may be retracted back into the body 110 as shown in FIG. 10D (or the body 110 may be removed from the uterus without retracting the plunger 165 and/or inner body 160). In some embodiments, the first and second actuators may be configured such that the inner body 160 is retracted as the plunger 165 is advanced. The plunger 165 may be extendable, relative to the inner body 160, to at least the distal end of the inner body 160, which ensures that the embryo is expelled from the inner body 160 (i.e. so that the embryo is prevented from remaining in the inner body 160).

Figure 1E:
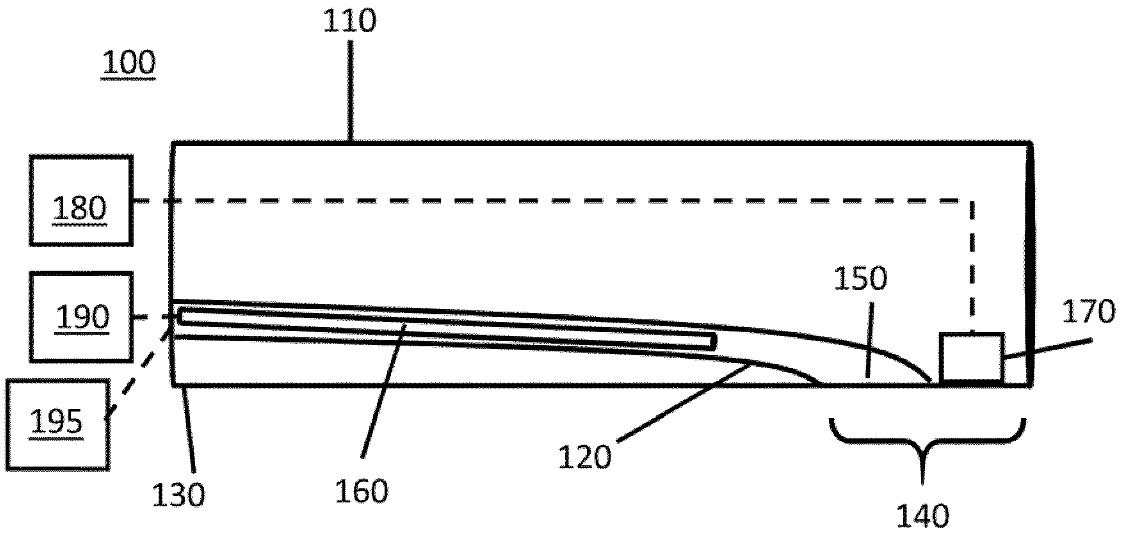
FIG. 1E shows a perspective view of another apparatus suitable for delivering a fertilized egg or embryo into a maternal uterine endometrium according to one or more embodiments shown and described herein.

Whilst FIG. 1D shows the measurement portion 170 and distal opening 150 of the body 110 at the distal tip of the body 110, in other embodiments the measurement portion 170 and distal opening 150 may be located at a side of the distal portion 140 of body 110, as shown in FIG. 1E. The lumen 120 comprises a gradually curved section proximal to the distal opening 150 of the body 110 in order to guide the inner body 160 laterally.

Figure 1F:
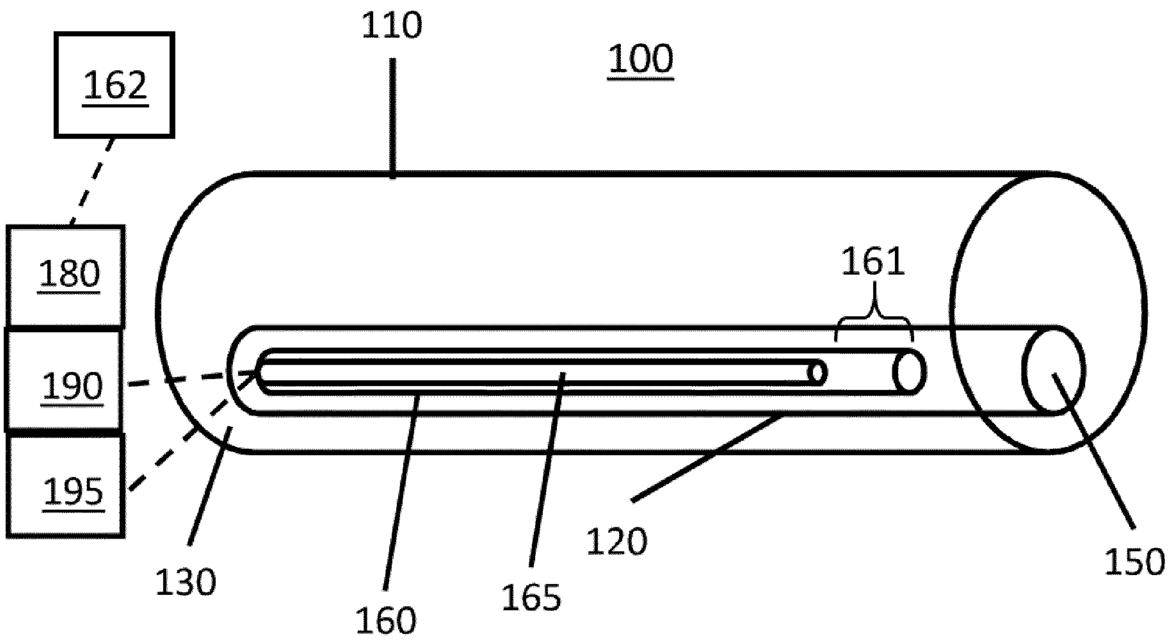
FIG. 1F shows a perspective view of another apparatus suitable for delivering a fertilized egg or embryo into a maternal uterine endometrium according to one or more embodiments shown and described herein.

FIG. 1D shows the measurement assembly comprising a measurement portion 170 disposed at the distal portion 140 of the body 110. In other embodiments the measurement portion 170 may be located at a different location (e.g. at a distal portion of the inner body 160) or the measurement assembly may be configured to interact with an element of the apparatus 100 in order to provide a qualitative or a quantitative measurement and may comprise any suitable element or elements, without the need of having a measurement portion within the measurement assembly. This is shown in the embodiment of FIG. 1F, wherein the apparatus 100 comprises an inner body 160 having a distal portion 161 comprising a distal end suitable for penetrating the endometrial epithelium. The apparatus 100 further comprises a body 110 (e.g. a catheter) configured to fit within a lumen of the female reproductive system. The body comprises a lumen 120 extending from a proximal end 130 of the body 110 to a distal portion 140 of the body 110 and having a distal opening 150 at the distal portion 140 of the body. The lumen 120 is configured to slidably receive the inner body 160. The apparatus 100 of FIG. 1F further comprises a measurement assembly 162. The measurement assembly 162 is configured to measure whether the apparatus 100 is in a first state indicating the distance between the distal end of the inner body 160 and the endometrial epithelium is greater than a predetermined distance (i.e. in the direction that the inner body is advanced from the distal opening 150 of the body 110), or a second state indicating that the distance between the distal end of the inner body 160 and the endometrial epithelium is equal to or less than a predetermined distance. The apparatus 100 of FIG. 1F further comprises an indicating device 180 coupled to the measurement assembly 162 and configured to indicate that the apparatus 100 is in the first state or the second state. The apparatus 100 also comprises a first actuator 190 operable to advance the inner body 160 out from the distal opening 150 of the body 110, and a second actuator 195 operable to expel a fertilized egg from the inner body (for example to advance a plunger 165).

In an embodiment, the distal portion 161 of the inner body 160 is electrically conductive, and the measurement assembly 162 is configured to make electrical contact with such distal portion 161 of the inner body 160. The measurement assembly thus provides an indication of the capacitance. In an embodiment, the first state is indicated by a capacitance measurement below a threshold value, and the second state is indicated by a capacitance measurement above the threshold value.

In a particular embodiment, the capacitance varies according to the variation of the distance between the distal portion 161 of the inner body 160 and the endometrial epithelium, i.e. the capacitance value changes depending on the proximity of the distal portion 161 of the inner body 160 with the endometrial epithelium. In an embodiment, the predetermined distance is zero (thus meaning contact between the distal portion 161 of the inner body 160 and the endometrial epithelium). In an embodiment, the capacitance value is measured by means of the measurement assembly 162, which comprises an electrical system which is electrically connected to the distal portion 161 of the inner body 160 for measuring the capacitance.

The use of the measurement assembly in combination with the indicating device assists in determining that the distal portion of the apparatus is within a predetermined distance such that the inner body can be advanced into the endometrial epithelium to deliver the fertilized egg. In embodiments wherein the indication provides information regarding the distance between the distal portion of body 110 and the endometrial epithelium, this may assist in avoiding direct contact between the distal portion of body 110 and the endometrial epithelium. Further, prematurely extending the inner body 160 into the uterus whilst the apparatus is still being positioned could cause damage to the inner body 160. Accordingly, the indicating device assists in identifying when it is appropriate to extend the inner body 160 out from the apparatus.

In embodiments wherein the indication provides information regarding the distance between the distal end of the inner body 160 and the endometrial epithelium, the use of the measurement assembly in combination with the indicating device assists in determining that the distal end of the inner body is within a predetermined distance such that the inner body can be further advanced into the endometrial epithelium to deliver the fertilized egg and/or that the inner body is in a position wherein the fertilized egg can be delivered. Accordingly, the indicating device assists in identifying when it is appropriate to deliver the fertilized egg.

In an embodiment, the apparatus 100 of FIGS. 1A-1F further comprises an imaging device, in particular a camera, not shown in the figures. In an embodiment, the camera is attached to the body 110 and moves together, as an integral device, with said body 110. In a particular embodiment, the camera is housed within the body 110.

Figure 2A:
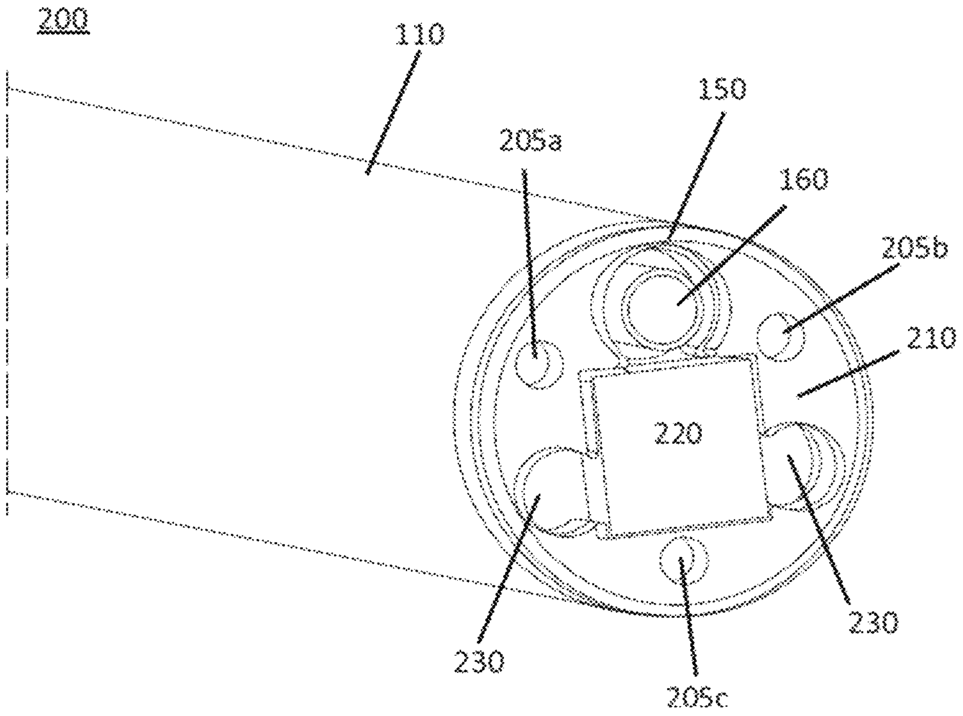
FIG. 2A shows a perspective view of measuring portion according to one or more embodiments shown and described herein.

FIG. 2A shows a perspective view of measuring portion according to one or more embodiments. The measuring portion comprises one or more light sources 205 proximal the distal opening 150 of the body 110. The one or more light sources 205 are configured to emit light from the distal portion of the body. The measuring portion further comprises one or more converging lenses 210 configured to focus the one or more light sources at a focal point away from the distal opening 150 of the body 110, and an imaging device 220 having a field of view including the focal point.

The one or more light sources 205 may be any suitable light source. For example, the light sources 205 may comprise one or more optical fibers, each extending through a respective lumen extending from a proximal end of the body (e.g. extending generally parallel to lumen 120) and connected to one or more light emitters at the proximal end of the body.

The one or more converging lenses 210 may be made of any suitable optically clear biocompatible material, such as a biocompatible resin, acrylics or polycarbonates. The lenses 210 may be attached to the body 110 by any biocompatible clear adhesives, such as biocompatible UV clear adhesives and or biocompatible cyanoacrylate adhesive. In the present embodiment, a single lens 210 is used, with a hole formed through the lens 210 such that the imaging device 220 is able to directly view the focal point. However, in other embodiments, the one or more lenses 210 may merely be located away from the imaging device 220. The focal point of the one or more lenses is selected to correspond to the predetermined distance.

The imaging device 220 may be any suitable imaging device. For example, the imaging device may comprise a camera such as a CMOS image sensor. When the imaging device 220 is a camera, the indicating device 180 may be a display configured to display the field of view to a user, or may comprise suitable hardware and/or software configured to receive image data from an imaging device and perform analysis of the image data to determine the state of the measurement assembly. Alternatively, the measurement assembly may comprise the software/hardware and provide the result of the analysis to the indicating device 180. The imaging device may instead comprise a fiberscope viewable by the user.

Whilst the apparatus 200 comprises three light sources 205*a*, 205*b* and 205*c*, in other embodiments the apparatus may comprise one, two or more than three light sources.

The apparatus 200 may also comprise one or more secondary light sources 230 configured to emit unfocussed light onto the endometrial epithelium from the distal portion of the body (i.e. the light does not pass through the lens 210). The colour of the secondary light source may be selected so as to allow the focused light to be distinguishable.

Figure 2B:
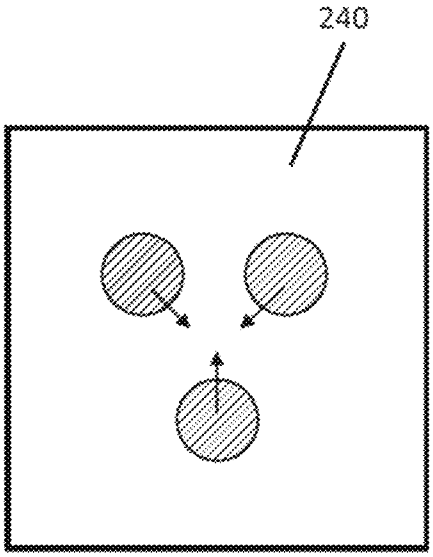
FIGS. 2B and 2C show views of the imaging device of the measurement assembly of FIG. 2A according to one or more embodiments shown and described herein.
Figure 2C:
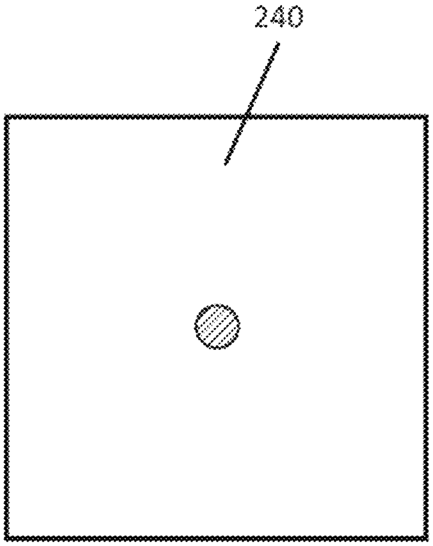

FIG. 2B illustrates a view 240 of the imaging device 220 as the body 110 is advanced towards a surface, wherein a distance of the distal opening 150 of the body 110 is greater than the predetermined distance. The surface is further away than the focal point and so the light sources appear as separated spots on the surface. As the body 110 is advanced, the spots converge, indicated by the arrows. FIG. 2C illustrates the view 240 when the body is advanced such that the light converges. If the body is further advanced closer than the focal point, the spots begin to diverge once again. The view of the imaging device 220 therefore serves as the indicating device 180 in indicating to a user that the distal opening 150 of the body 110 is at the predetermined distance. Alternatively, imaging data may be analysed by the indicating device 180 against predetermine criteria to determine if the focal point has been reached. For example, known object tracking algorithms can be implemented to track the location of the three spots of light, to determine when the spots are close enough to be considered as converged.

Where two light sources 205, a similar converging behaviour occurs in the view 240 such that the focal point can be observed. The provision of three or more light sources 205 provide easier identification of the focal point in the case that the surface of the endometrial epithelium is uneven, or when the plane containing the three light sources is not parallel to the surface of the endometrial epithelium.

In an embodiment where only one light source 205 is used, the focal point can still be determined from the view of the imaging device 220. Specifically, the view of the imaging device 220 can be calibrated such that the xy position of the spot from the light source at the focal point is known. This can be used to provide a comparison point on an eyepiece of a fiberscope or on a digital display, or can be used as criteria in an image analysis algorithm.

Figure 3:
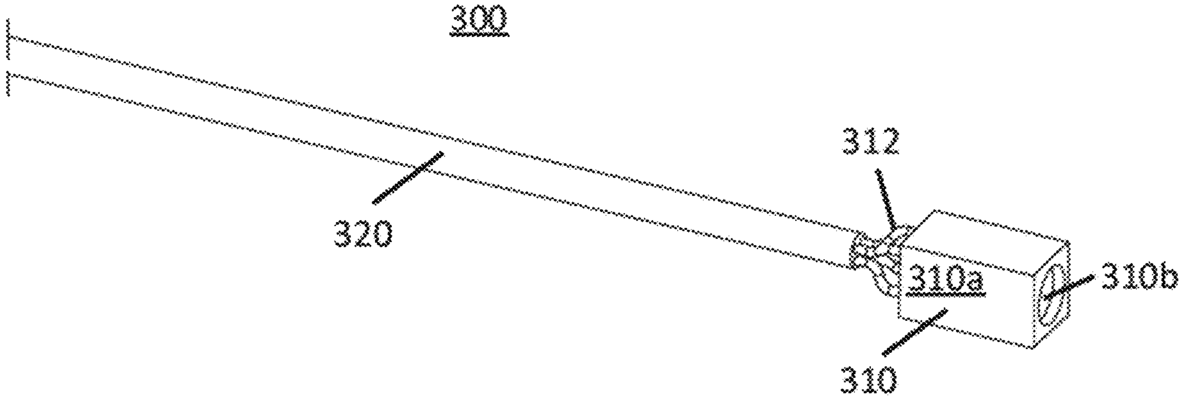
FIG. 3 shows a perspective view of an imaging assembly comprising an imaging device for use as part of a measurement assembly in one or more of the embodiments shown and described herein.

FIG. 3 shows a perspective view of an imaging assembly 300 comprising an imaging device 310 that may be used as part of a measurement assembly in one or more of the embodiments disclosed herein. The imaging device 310 comprises a CMOS chip located inside housing 310*a* and lens 310*b* at a distal end of the imaging assembly 300 for receiving focusing light from the endometrial epithelium onto the CMOS chip. The imaging assembly 300 further comprises a plurality of wires or cables 312 for electrically connecting the CMOS chip to a proximal end of the apparatus to provide the necessary power and signal communications (e.g. to a power source and image processor at a proximal end of the apparatus) to operate the imaging assembly 300. For example, the imaging assembly 300 may comprise a plurality (e.g. four) coaxial cables 312, each cable comprising an outer conductor and an inner coaxial conductor inside the outer conductor. The coaxial wiring is preferred to reduce noise in the received signal and therefore to achieve a clearer image. Each cable 312 may individually pass through a separate lumen extending through the body 110 from the distal portion 140 to the proximal end 130. Alternatively, one or more (or all) of the cables 312 may pass through a single insulating shroud 320 that extends through the body 110 from the distal portion 140 to the proximal end 130. The insulating shroud 320 may be any electrically insulating material, for example PVC. The proximal portions of the cables are electrically connected to the various components at the proximal end of the apparatus to provide suitable power and signal connections to the CMOS chip.

Figure 4:
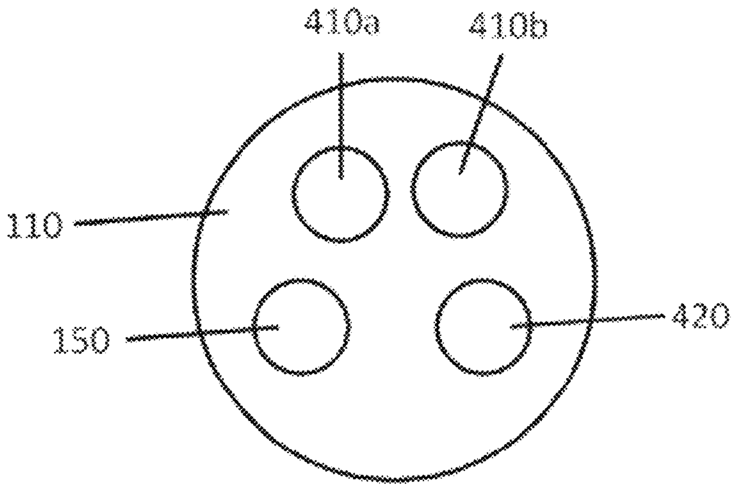
FIG. 4 shows a front view of a measuring portion according to one or more embodiments shown and described herein.

FIG. 4 shows a front view of a measuring portion according to one or more embodiments. The measurement assembly of FIG. 4 comprises a distance measuring probe at a proximal end of the apparatus, and configured to emit and receive a signal at the distal portion 140 of the apparatus. The probe could be any distancing probe configured to calculate distance from any suitable signal, for example any suitable optical, acoustic, electrical or other signal. The probe emitter/receiver terminate at openings 410*a* and 410*b* proximal the distal opening 150. In some embodiments, the signal may be emitted and received from a single opening 410 rather than a pair of openings. The probe may be, for example, an optical coherence tomography (OCT) probe including an OCT fiber bundle terminating proximal to the distal opening 150. The OCT scanning probe is configured to calculate the distance of the distal opening to a portion of the endometrial epithelium. For example, the OCT probe may comprise a light signal emitter at the proximal end of the apparatus. The emitter may emit a light signal that is split into a reference path having a known length and a second path that is emitted to (and reflected from) the endometrial epithelium. Light reflected from the reference path and the second path is recombined and detected at the proximal end of the apparatus (i.e. by the indicating device 180). The resulting interference pattern may be processed to determine density changes in the second path which can be interpreted as surfaces. The distance to each of the density changes can therefore be determined, including the distance to the surface of the endometrial epithelium.

The apparatus 400 may optionally also comprise a fiberscope 420. The indicating device 180 is configured to compare the measured distance to the predetermined distance and to indicate whether the measured distance corresponds to the opening being farther or close than a predetermined distance to the endometrial epithelium.

In one embodiment, the measuring portion 170 may comprise any suitable acoustic distance-measuring device. The acoustic device may emit acoustic signals to the endometrial epithelium, from the distal portion 140 of the apparatus 100 in response to electrical control signals transmitted through the body 110 from the proximal end of the apparatus. The reflected acoustic signals may be converted into an electrical signal by the acoustic device and transmitted to the indicating device 180 for processing, from which the distance to the endometrial epithelium can be calculated.

In another embodiment, the measurement assembly may comprise a camera proximal the distal opening 150 of the body 110 and configured to view a portion of the endometrial epithelium, wherein the depth of field of the camera has a predetermined value defined by nearest and the farthest objects that are in acceptably sharp focus, such that when the image is in focus, the distal opening is at the predetermined distance to the endometrial epithelium. The indicating device 180 may comprise a display for displaying an image captured by the camera. Alternatively, the indicating device 180 may comprises suitable software and/or hardware for processing the image data of the camera to determine whether the image is in focus (for example by measuring the sharpness of the image using known image analysis methods). Alternatively, the measurement assembly may comprise the software/hardware and provide the result of the analysis to the indicating device 180.

In another embodiment, the measurement assembly may comprise a confocal probe.

In yet another embodiment, the measurement assembly may comprise a laser probe comprising an optical fiber terminating at opening 410 proximal to the distal opening 150 of the body 110. The laser probe is configured to measure the time of flight of laser radiation transmitted to the endometrial epithelium and reflected back to the laser probe through the optical fiber and calculate the distance to the endometrial epithelium from the time of flight value. The indicating device 180 is configured to compare the distance measured by the laser probe (taking into account the distance travelled by the radiation along the optical fiber) to the predetermined distance and to indicate whether the measured distance corresponds to the opening being farther or at/closer than a predetermined distance to the endometrial epithelium.

In another embodiment, the measurement assembly may comprise an ultrasound probe configured to transmit and receive sound waves from one or more openings 410 towards the endometrial epithelium, the measurement assembly configured to calculate the distance of the distal opening to the endometrial epithelium. The indicating device 180 is configured to compare the distance measured by the ultrasound probe (taking into account the distance travelled by the sound waves along the apparatus) to the predetermined distance and to indicate whether the measured distance corresponds to the opening being farther or at/closer than the predetermined distance to the endometrial epithelium.

Figure 5A:
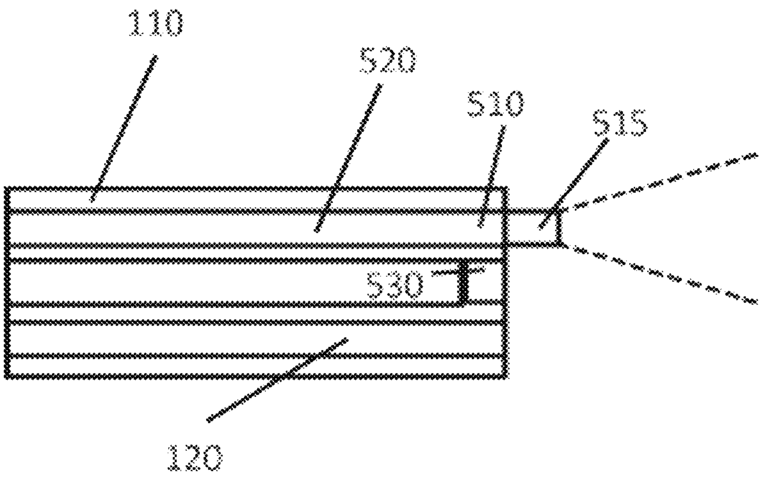
FIG. 5A shows a cross-sectional side view of a measuring portion according to one or more embodiments shown and described herein.

FIG. 5A shows a cross-sectional side view of a measuring portion according to another embodiment. The measuring portion comprises a light source 510 having a fixed aperture configured to illuminate a shape on the endometrial epithelium (for example a circular region), and an imaging device 530 having a field of view 540 including the illuminated region. As discussed previously, the light source 510 may be any suitable light source and may be connected to a light emitter at a proximal end of the apparatus via an optical fiber extending through a lumen 520 in the body 110. A narrower aperture of the light source may be achieved by providing an opaque cylindrical body 515 which extends distally from the light source 510. The opaque body may be, for example, hypodermic tubing fixed to the light source 510 through which the light may be emitted.

Figure 5B:
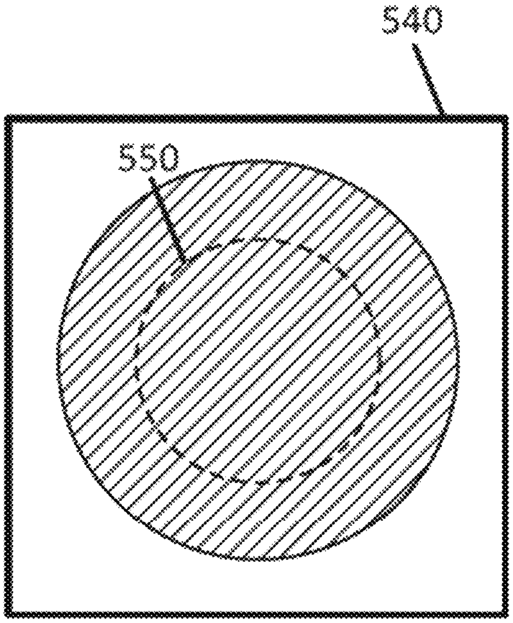
FIGS. 5B and 5C show views of the imaging device of the measurement assembly of FIG. 5A according to one or more embodiments shown and described herein.
Figure 5C:
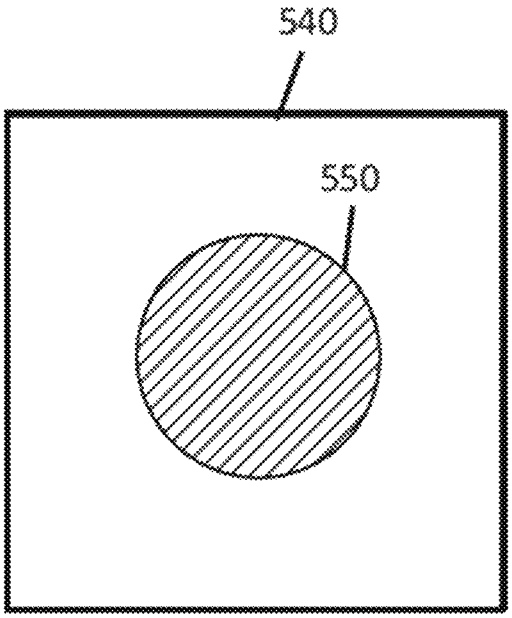

When the shape appearing in the view of the imaging device 530 is bigger than a predetermined size, this indicates the distance between the distal opening and the endometrial epithelium is greater than a predetermined distance. When the viewed shape matches or is smaller than the predetermined size, this indicates the distance between the distal opening and the endometrial epithelium is equal to or less than a predetermined distance. The view 540 of the imaging device may be displayed on a display comprising a comparison overlay 550, as displayed in FIGS. 5B and 5C. In FIG. 5B, the distal opening is further from the endometrial epithelium than the predetermined distance. In FIG. 5B, the distal opening is at the predetermined distance to the endometrial epithelium. Alternatively, imaging data may be analysed by the indicating device 180 against predetermine criteria to determine the size of the illuminated shape in the view of the imaging device. For example, known object tracking algorithms can be implemented to track the size of the shape, to determine when the shape is small enough to be considered as corresponding to the predetermined distance being reached.

FIG. 6 shows a front view of a measuring portion according to one or more embodiments. The measuring portion comprises a stereo camera 410*a*, 410*b*, and a light source 420. The stereo camera is configured to image the endometrial epithelium. The measurement assembly and/or indicating device may comprise software/hardware configured to perform a stereo algorithm to determine one or more depths of points in the stereo image. The distance to the endometrial epithelium is then calculated from the one or more depths. In particular, the cameras are positioned at a known angle to each other but pointed at the same target. The software combines and analyses the image data to perform depth measurements of the surface of the endometrial epithelium.

FIG. 7A shows a perspective view of a measuring portion according to one or more embodiments. FIG. 7B shows a cross-sectional side view taken along the line A-A of FIG. 7A. The measuring portion comprises a light source 720 configured to illuminate the endometrial epithelium, and a rigid protrusion 730 positioned to cast a shadow onto the endometrial epithelium. The measuring portion further comprises an imaging device 710 having a field of view 760 which includes the shadow. The protrusion 730 is positioned relative to the light source 720 and the imaging device 710 such that when an edge of the viewed shadow crosses a predetermined location in the field of view, the measurement assembly transitions from the first state to the second state. The protrusion may be made of any suitable material which remains rigid as the apparatus is advanced through the uterus, for example stainless steel wire or biocompatible plastic such as peek or FEP or PTFE or PI. It may be attached to the distal portion of the body 110 by any suitable means, such as any biocompatible adhesive (for example a UV curable clear or cyanoacrylate adhesive).

The light source 720 may be any suitable light source. For example the light source may be optically connected to a light emitter at a proximal end of the apparatus via an optical fiber extending through a lumen 750 of the body 110. Likewise, the imaging device may be any suitable device such as a fiberscope connected to a proximal end via lumen 740 of body 110, or it may comprise a camera electrically connected to a power source and signal receiver at a proximal end of the apparatus through a lumen 740 extending through body 110.

The view may be displayed on a display comprising a comparison overlay 770, as shown in FIGS. 7C and 7D, which shows exemplary views of the shadow cast on the endometrial epithelium as the apparatus is advanced. In FIG. 7C, the distal opening is further away from the endometrial epithelium than the predetermined distance. In FIG. 7D, the apparatus has been advanced closer to the endometrial epithelium and the edge of the shadow crosses the overlay 770 and the measurement assembly is within the predetermined distance. Alternatively, imaging data may be analysed by the indicating device 180 against predetermine criteria to determine the size of the illuminated shape in the view of the imaging device. For example, known object tracking algorithms can be implemented to track the position of the shadow in the field of view (for example using known edge detection algorithms), to determine when the position of the shadow indicates that the predetermined distance has been reached.

Figure 8A:
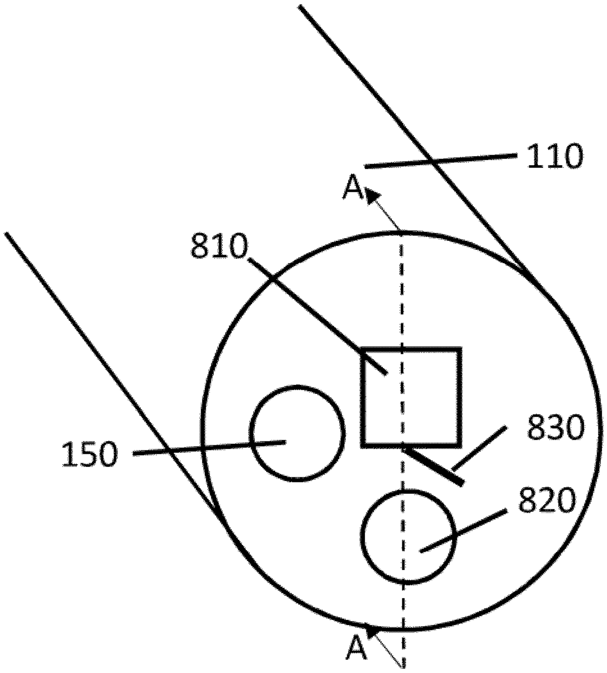
FIG. 8A shows a perspective view of a measuring portion according to one or more embodiments shown and described herein.
Figure 8B:
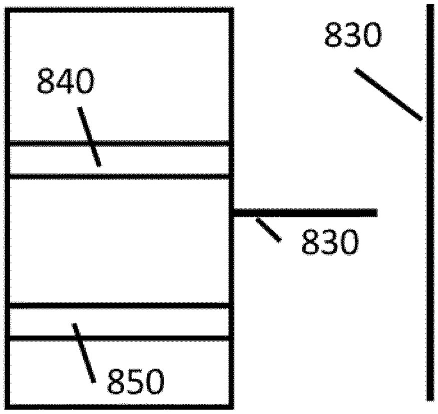
FIGS. 8B and 8C show cross-sectional side view of the measuring portion shown in FIG. 8A taken along the line A-A in different configurations.

FIG. 8A shows a perspective view of a measuring portion according to one or more embodiments. FIG. 8B shows a cross-sectional side view taken along the line A-A of FIG. 8A. The measuring portion comprises a light source 820 configured to illuminate a resiliently deformable protrusion 830 configured to extend towards the endometrial epithelium. The measuring portion further comprises an imaging device 810 having a field of view of the protrusion. The protrusion being undeformed (i.e. in its relaxed state) indicates that the measurement assembly is in the first state and the protrusion being deformed indicates the second state. The indicating device may comprise a display coupled to the imaging device such that the protrusion 830 is viewable by an operator. Alternatively, imaging data may be analysed by the indicating device 180 against predetermine criteria to determine whether the protrusion has deformed. For example, known object tracking algorithms can be implemented to track the shape of the protrusion (for example using known edge detection algorithms), to determine when the deformation of the protrusion indicates that the predetermined distance has been reached.

Figure 8C:
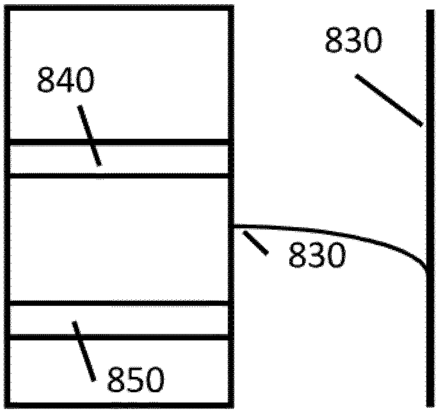

FIG. 8B shows a configuration wherein the distal opening 150 is farther from the endometrial epithelium than the predetermined distance. FIG. 8C shows a configuration wherein the distal opening 150 is closer to the endometrial epithelium than the predetermined distance, wherein the protrusion is deformed due to abutting the endometrial epithelium.

The light source 820 may be any suitable light source. For example, the light source may be optically connected to a light emitter at a proximal end of the apparatus via an optical fiber extending through a lumen 850 of the body 110. Likewise, the imaging device may be any suitable device such as a fiberscope connected to a proximal end via lumen 840 of body 110, or it may comprise a camera electrically connected to a power source and signal receiver at a proximal end of the apparatus through a lumen 840 extending through body 110.

The protrusion 830 may be made of any suitable material which is deformable as the apparatus is advanced towards the endometrial epithelium as the protrusion 830 abuts the endometrial epithelium, without penetrating the endometrial epithelium. For example, it may be made of a stainless steel wire or biocompatible plastic such as PEEK, FEP, PTFE or PI. It may be attached to the distal portion of the body 110 by any suitable means, such as biocompatible adhesive (e.g. a UV curable clear or cyanoacrylate adhesive). The protrusion 830 may be configured to extend in the direction in which the apparatus is intended to be advance towards endometrial epithelium, and the length of the protrusion 830 may correspond to the predetermined distance.

In yet another embodiment, the measurement portion may comprise a pressure sensor configured to measure the pressure exerted on the distal portion of the body 110 by the endometrial epithelium when the distal portion 140 abuts it. When the pressure signal is above a predetermined threshold, the distal portion is considered to be at the endometrial epithelium. For example, it may be acceptable to exert a low amount of pressure on the endometrial epithelium without causing damage to the endometrial epithelium. Any suitable pressure sensor may be used, such as an optical pressure sensor configured to measure the optical change in a light signal caused by deformation of a sensor chip at the distal end of the apparatus.

The pressure sensor may have appropriate electrical connections to a proximal end of the apparatus through one or more lumens 175 extending through the body 110. For example, the pressure sensor may be electrically connected to the indicating device 180, and the indicating device may comprise suitable hardware and/or software to analyse whether the electrical signal of the pressure sensor indicates that the endometrial epithelium has been reached. The indicating device 180 may then indicate to the user or to a controller that the predetermined distance (of zero) has been reached. The indicating device 180 may optionally also be configured to analyse whether the electrical signal of the pressure sensor indicates that the pressure exerted on the endometrial epithelium is higher than a second threshold, indicating that damage may be caused to the endometrial epithelium. The indicating device 180 may then indicate to the user or the controller that the acceptable level of pressure has been exceeded.

In yet another embodiment, the measurement portion may comprise a capacitive sensor configured to measure the capacitance, preferably as the distance between the distal portion of the body and the endometrial epithelium changes. The capacitive sensor is located on the part of the distal portion of the body which is configured to impact the endometrial epithelium first as the body is advanced and the measurement assembly is configured to provide an indication of the capacitance. When the capacitance is above a predetermined threshold, the distal portion of the body is considered to be in contact with the endometrial epithelium. Instead of a capacitance sensor, an electrically conductive element may be used, the electrically conductive element being located at least on the part of the distal portion of the body which is configured to impact the endometrial epithelium first as the body is advanced. The measurement assembly may comprise an electrical system which is electrically connected to the electrically conductive element for measuring the capacitance. The electrically conductive element may be an electrically conductive portion of the body or may be an element attached to the distal portion of the body for capacitance measurement purposes. In an embodiment, the electrically conductive element is an electrically conductive wire that extends along at least a portion of the body, preferably along the whole length of the body.

In yet another embodiment, the measurement assembly may comprise several of the aforementioned embodiments, thus combining different types of measurements based on different measurement techniques.

In yet another embodiment, the measurement assembly comprises a measurement portion disposed at the distal portion of the body, the measurement assembly being configured to measure whether the apparatus is in a first state indicating that a distance between the distal portion of the body and the endometrial epithelium is greater than a predetermined distance, or a second state indicating that a distance between the distal portion of the body and the endometrial epithelium is equal to or less than a predetermined distance; wherein the measurement assembly is further configured to measure whether the apparatus is in a third state indicating that a distance between the distal end of the inner body and the endometrial epithelium is greater than a predetermined distance, or a fourth state indicating that a distance between the distal end of the inner body and the endometrial epithelium is equal to or less than a predetermined distance; and wherein the indicating device is further configured to indicate that the apparatus is in the third state or the fourth state. In an embodiment, the measurement assembly is configured to make electrical contact with a distal portion of the inner body which is electrically conductive, and to provide an indication of the capacitance, wherein the third state is indicated by a capacitance measurement below a threshold value and the fourth state is indicated by a capacitance measurement above the threshold value; wherein preferably the predetermined distance is zero. This embodiment provides information of both the positioning of the distal portion of the body and the positioning of the distal end of the inner body, thus allowing more precise control of the implantation process.

In some embodiments, the apparatus 100 may further comprise a steering mechanism configured to steer a distal portion of the body 110 (i.e. a portion of the body which is configured to extend into the uterus), and a third actuator for operating the steering mechanism which may be manually actuated by a user or actuated by one or more motors. Any mechanism suitable for steering the body 110 may be used. The body 110 may be slidable relative to the steering mechanism and third actuator, such that it may be advanced towards the endometrial epithelium without having to advance the steering mechanism.

Figure 9A:
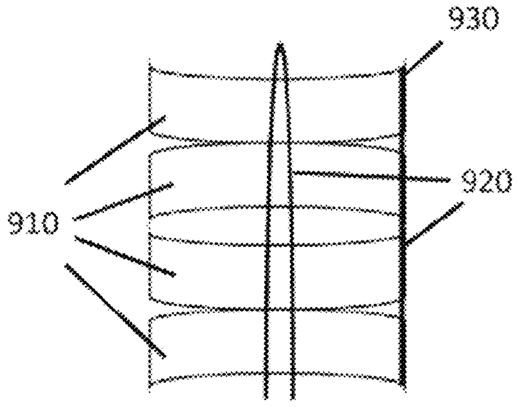
FIG. 9A shows a side view of a steering mechanism according to some embodiments shown and described herein.

FIG. 9A shows a side view of a steering mechanism configured to steer a distal portion of the body 110 according to some embodiments. The steering mechanism comprises a plurality of connected rings 910 forming a tube wall configured to at least partially surround a portion of the body 110. Specifically, the rings 910 are sized to receive the body 110 inside the tube wall, and may slidably receive the body 110. The mechanism further comprises at least one cable 920 extending longitudinally along the tube wall and attached to a distal end 930 of the tube wall. For example, the at least one cable may extend longitudinal along the inner or outer side of the tube wall or may extend longitudinally through the tube wall. The mechanism may comprise a plurality of said cables located at different circumferential positions about the tube wall. The connected rings 910 may be connected by the cables 920 alone. The connected rings 910 may further be configured to maintain a predetermined alignment by comprising a set of interlocking features which inhibit the rings 910 from rotating about the longitudinal axis. The steering mechanism shown in FIG. 9A comprises a plurality of connected rings 910 which are pivotable about each other. In other words, the connected rings are undulated such that neighbouring rings abut at a tangential contact point. This enables the rings 910 to roll about each other to steer the body 110 when one of the cables 920 are retracted by the third actuator (not shown). The circumferential position of the tangential contact points about which the ring 910 roll may be varied along the length of the steering mechanism. For example, sequential circumferential contact points may be offset by 90 degrees in order to accommodate rolling in two perpendicular directions by a plurality of cables. Preferably, the steering mechanism comprises two pairs of said cables, each pair comprising radially opposing cables, in order to provide steering in a plurality of directions. Such a configuration is shown in FIG. 9C, which is a top view of such a steering mechanism.

The connected rings shown in FIG. 9A may be made of any suitable material such as medical grade injection mouldable or 3D printed plastic resin such as ABS, PET, DELRIN or PTFE. The cables 920 may be made of, for example, stainless steel and threaded through holes formed in the walls of the connected rings forming the tube wall. The cables 920 may each extend through a pair of holes in the connected rings and be looped at the distal end 930 as shown in FIGS. 9A and 9C. The third actuator may be any suitable actuator for contracting the one or more cables.

Figure 9B:
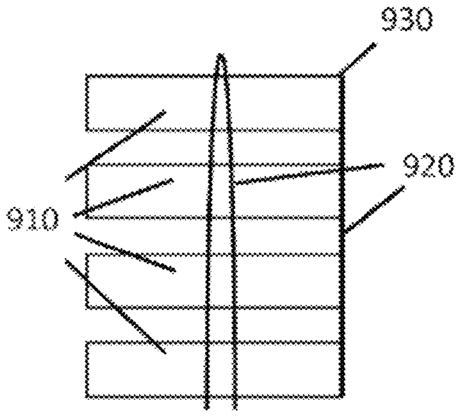
FIG. 9B shows a side view of another steering mechanism according to some embodiments shown and described herein.
Figure 9C:
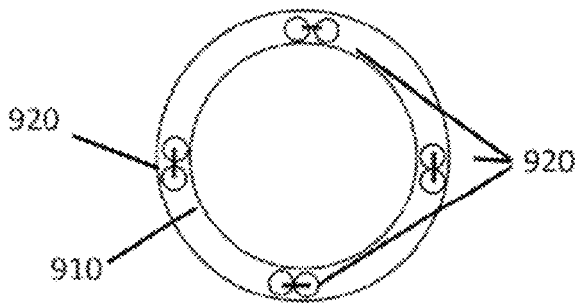
FIG. 9C shows a top view of the steering mechanisms shown in FIG. 9A or 9B.

FIG. 9B shows a side view of a steering mechanism according to an alternative embodiment. The steering mechanism comprises a plurality of connected rings 915 forming a tube wall configured to at least partially surround a portion of the body 110. Specifically, the rings 915 are sized to receive the body 110 inside the tube wall, and may slidably receive the body 110. The mechanism further comprises at least one cable 920 extending longitudinally through the tube wall and attached to a distal end 930 of the tube wall. The plurality of connected rings 910 are rings of a compressible tube or spring. When one of the cables is retracted by the third actuator (not shown), the tube or spring is compressed on the side of the retracted cable such that the steering mechanism is steered towards the contracted side. As the tube is compressible, the tension force is partly counteracted such that the resulting curve of the mechanism shown in 9B may be less than for the embodiment shown in FIG. 9A for a given tensioning force. Once again, preferably, the steering mechanism comprises two pairs of said cables, each pair comprising radially opposing cables, in order to provide steering in a plurality of directions, as shown in FIG. 9C.

The connected rings shown in FIG. 9B may be a compressible tube or spring made of any suitable material such as FEP, PTFE. The cables may be made of any suitable material such as stainless steel and threaded through holes formed in the walls of the connected rings forming the tube wall. The cables 920 may each extend through a pair of holes in the connected rings and be looped at the distal end 930 as shown in FIGS. 9A and 9C. The third actuator may be any suitable actuator for contracting the one or more cables.

Figure 9D:
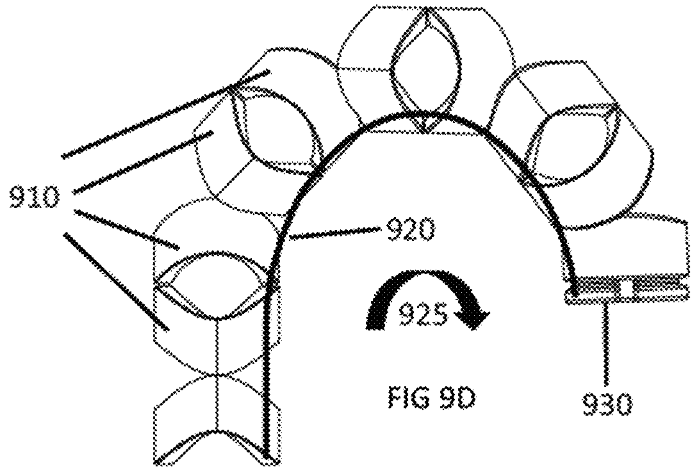
FIG. 9D shows a side view of a steering mechanism with a cable in a retracted position according to one or more embodiments shown and described herein.

FIG. 9D shows a side view of a steering mechanism when one of the cables has been retracted, such that the steering mechanism is steered in the direction illustrated by arrow 925.

Figure 9E:
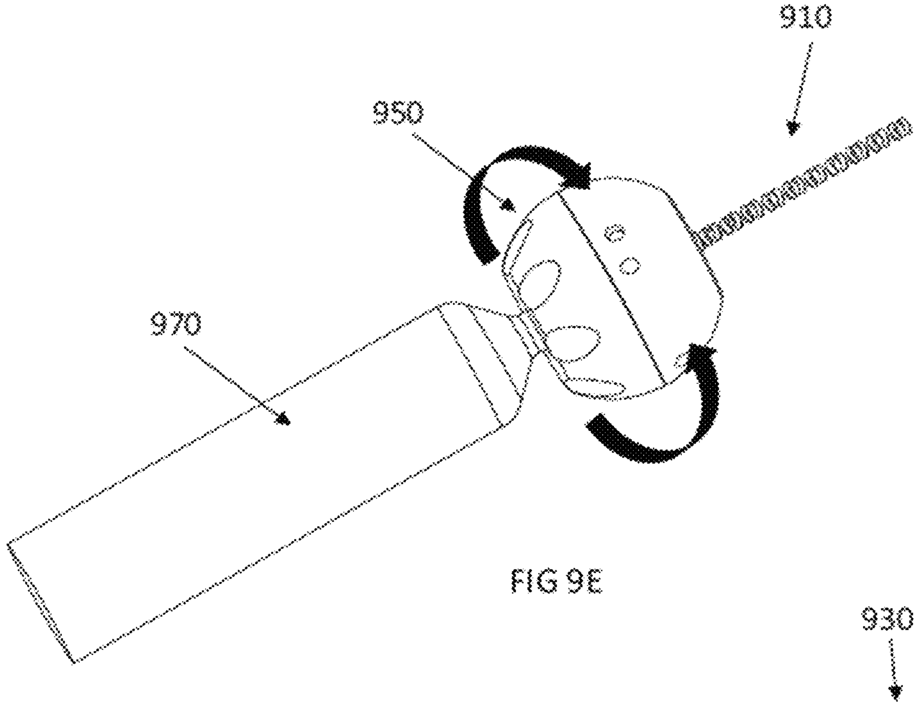
FIG. 9E shows a perspective view of a third actuator according to some embodiments shown and described herein.
Figure 9F:
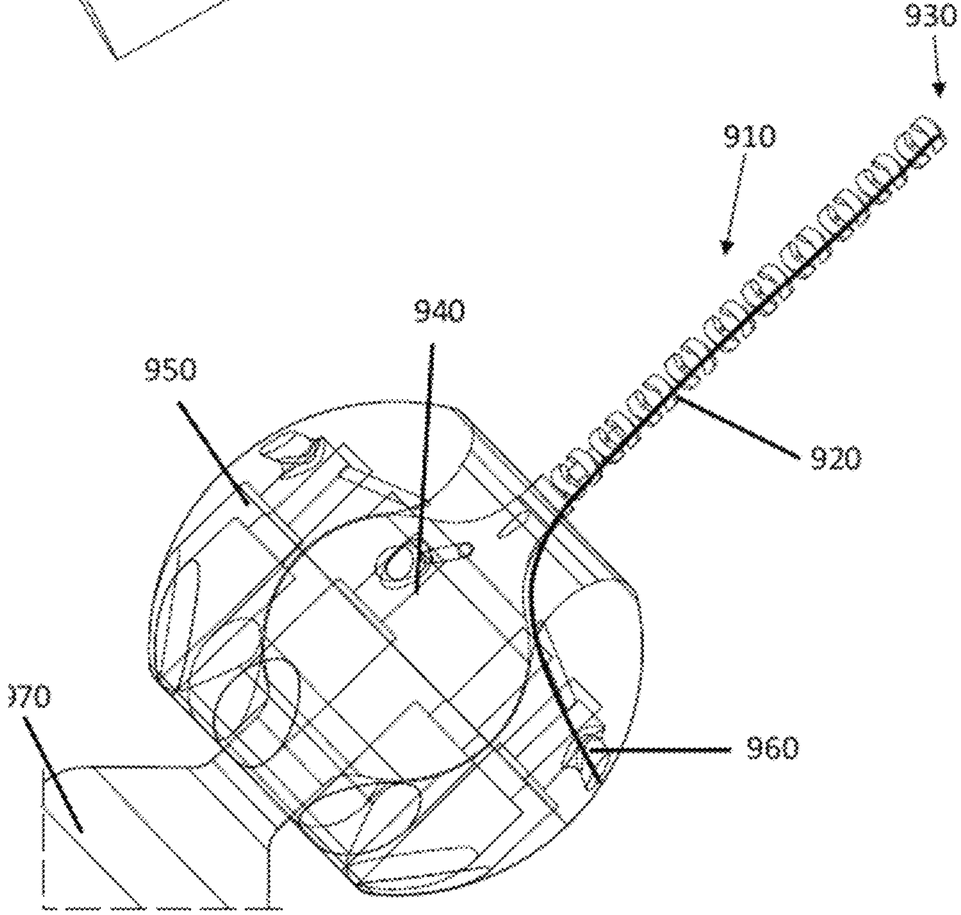
FIG. 9F shows a perspective view of the third actuator shown in FIG. 9E with the outer shell depicted as transparent.

FIG. 9E shows a perspective view of the third actuator according to some embodiments. FIG. 9F shows a perspective view of the third actuator shown in FIG. 9E with the outer shell 950 depicted as transparent. The third actuator comprises an inner element 940 and an outer shell 950 housing the inner element 940. Each of the at least one cables 920 are fixed to the outer shell at a proximal portion 960, for example by welding, adhesive, or about a fixed winch. The inner element 940 is fixedly connected to the tube wall 910 either directly or indirectly via one or more intermediate components. The outer shell 950 is rotatable relative to the inner element 940. Optionally, a handle 970 may be fixed to the inner element 940 through the outer shell 950. Rotating the outer shell 950 about the inner element 940 causes one of the cables 920 to be retracted, which steers the tube wall in a certain direction as discussed above. The body may extend through the handle 970 and the inner element 940 such that it may be advanced through the steering mechanism.

Figure 9G:
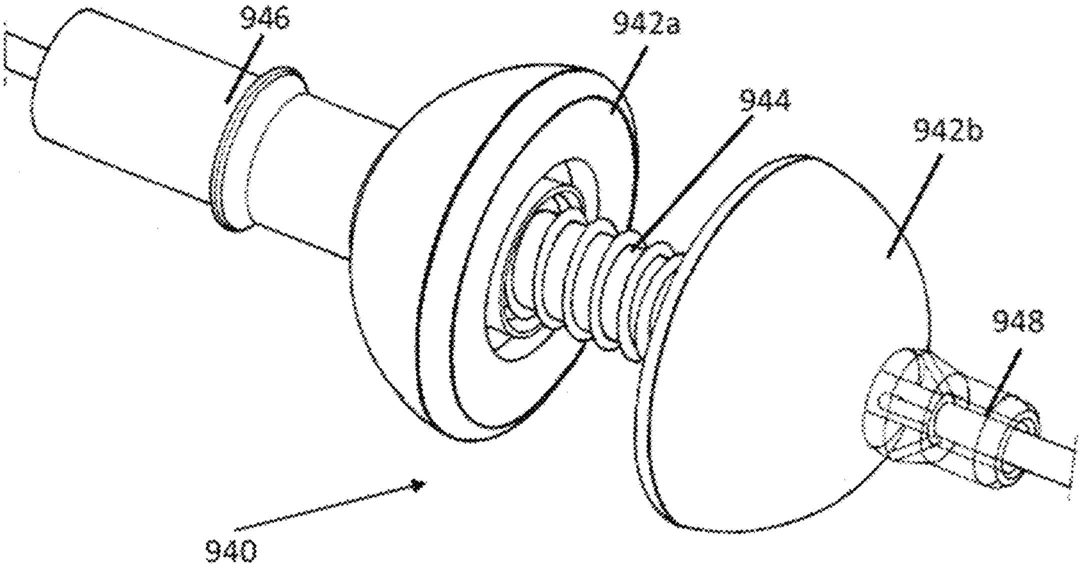
FIG. 9G shows a perspective view of an inner element of the steering mechanism according to some embodiments shown and described herein.

FIG. 9G shows a perspective view of the inner element according to some embodiments. The inner element 940 may comprise one or more components which are biased to abut the outer shell 950. For example, the inner element 940 may comprise two hemispheres 942*a*, 942*b*, which are biased away from each other to abut the inner surface of the outer shell 950. The biasing causes a frictional fit to be obtained between the inner element 940 and outer shell 950, such that they may only slide relative to each other when a sufficient force is applied, meaning that once a desired direction of the steering mechanism is achieved, it may be maintained in position by the third actuator. The inner element may be connected to the handle via a handle connector 946, and may be connected to the tube wall via an intermediate portion 948. The intermediate portion 948 may be incompressible and the cables 920 may be threaded through the intermediate portion and to the tube wall.

Figure 9H:
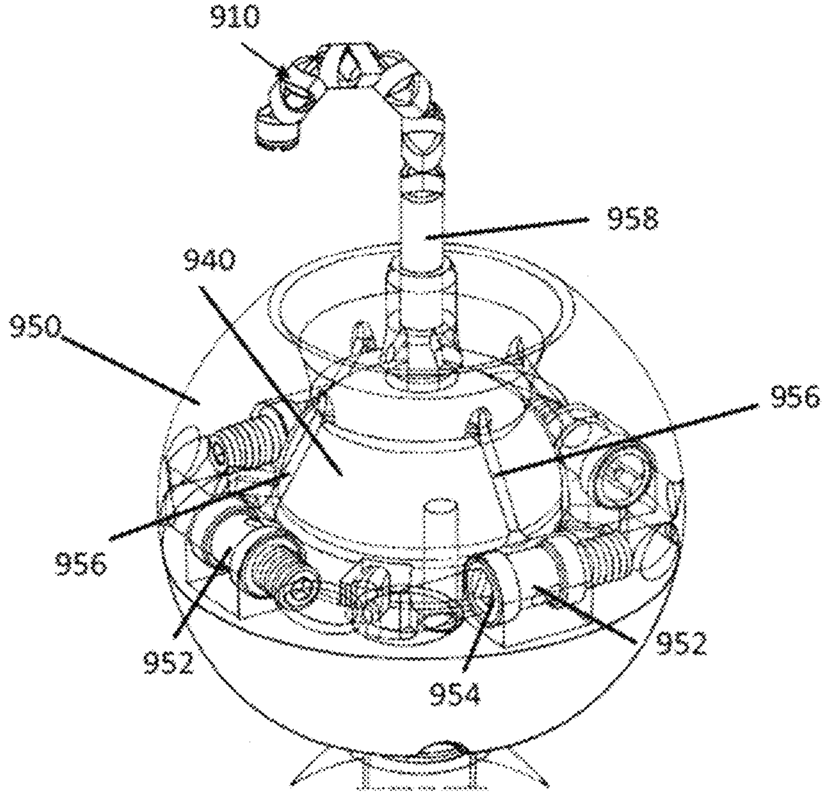
FIG. 9H shows a perspective view of a steering mechanism according to some embodiments shown and described herein, with the outer shell illustrated as partially transparent.

FIG. 9H shows a perspective view of a steering mechanism according to some embodiments, with the outer shell 950 illustrated as partially transparent. The steering mechanism of FIG. 9H also comprises an inner element 940 and an outer shell 950 housing the inner element 940 and rotatable relative to inner element 940, as described above. The steering mechanism may also comprise the handle 970. Further, each of the cables 920 are fixedly connected to the outer shell via a winch 952 (i.e. the cables are wound to the winch). The winch may be wound or unwound using an adjuster 954 (for example a flat head adjuster) which is accessible externally to the outer shell 950, meaning that the default tensions for each cable 920 may be calibrated after assembly of the steering mechanism. The rings 910 forming the tube wall may be fixedly connected to the inner element 940 via an inflexible tubular intermediate 958. The tubular intermediate 958 may be of any suitable length. For example, in embodiments where the outer catheter is used, the tubular intermediate 958 may be configured to extend through any inflexible parts of the outer catheter.

The cables 920 may extend through channels 956 formed in the inner surface of outer shell 950, and thus avoid contact with the inner element 940, avoiding damage to the cables as the outer shell rotates relative to the inner shell 940. The cables 920 may extend from the channels 956 and through lumens formed in the wall of the tubular intermediate 958, and to the tube wall.

The outer shell 950, inner element 940, handle 970, winches 952 and tubular intermediate 958 may be made of medical grade injection moldable or 3D printed plastic resin such as ABS, PET, DELRIN or PTFE.

The steering mechanism may instead be electronically controlled. For example, the steering mechanism shown in FIG. 9H may comprise an electronic controller fixed to the inner element 940, and comprising motors for actuating movement of the outer shell 950 relative to the inner element 940. Alternatively, a steering mechanism may comprise a plurality of connected rings forming a tube wall configured to at least partially surround a portion of the body, and at least two opposing cables extending longitudinally through the tube wall and attached to a distal end of the tube wall, wherein the cables are connected to a motor configured to contract the cables to steer the steering mechanism.

The tube wall of the steering mechanism is sized to slidably receive the body 110. The outer diameter of the tube wall may be about 1.4 mm to 1.8 mm or about 1.5 mm to 1.7 mm, for example 1.6 mm. In embodiments where the steering mechanism is used, the body 110 may be configured to advance beyond the end of the steering mechanism by about 20 mm to 40 mm, for example about 30 mm.

Figure 11:
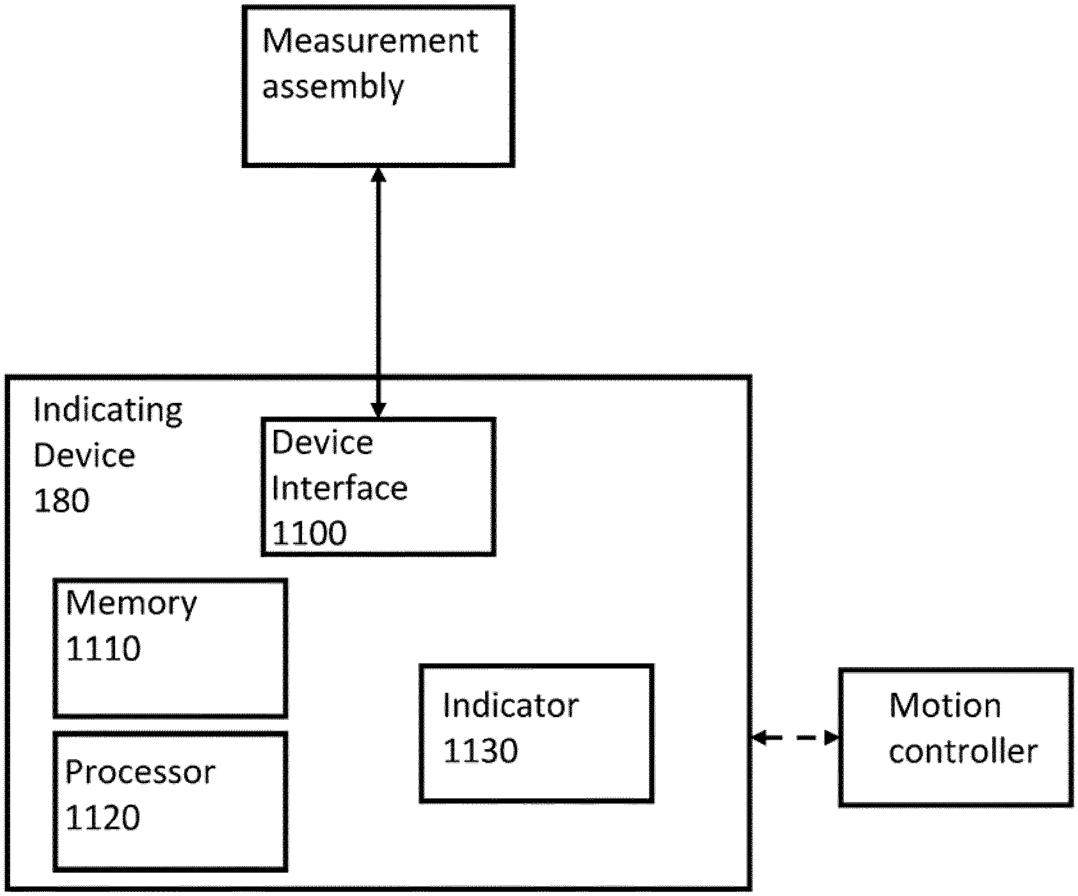
FIG. 11 shows a diagram of an indicating device according to one or more embodiments shown and described herein.

FIG. 11 shows a diagram of an indicating device 180 which may be used when the output of the measurement assembly is a signal (for example if the measurement assembly comprises a camera or distance measuring probe). The indicating device comprises a device interface 1100 configured to communicate with (i.e. send and receive signals from) the measurement assembly. The indicating device further comprises a memory 1110, processor 1120 and indicator 1130. It will be appreciated than any suitable computing system may be used for the indicating device 180 and that the device shown in FIG. 11 is one of many devices that could be used. For example, a distributed computer system may be used, for example comprising one or more servers or client computing systems, using any known distributed computing technique. In some examples, a general-purpose computer or any other processing system may be used to implement the methods disclosed herein. Furthermore, the steps disclosed below may be implemented in software, hardware, or any combination of these to achieve the same steps.

It will be appreciated by the skilled person that the indicating device of FIG. 11 may be powered by any suitable powering means. The memory 1110 may comprise one or more volatile or non-volatile memory devices, such as DRAM, SRAM, flash memory, read-only memory, ferroelectric RAM, hard disk drives, floppy disks, magnetic tape, optical discs, or similar. Likewise, the processor 1120 may comprise one or more processing units, such as a microprocessor, GPU, CPU, multi-core processor or similar. The device interface 1100 may comprise wired connections, such as optic, fiber-optic, ethernet or similar, or any suitable wireless communication.

In the case of the measurement assembly making a quantitative measurement (e.g. comprising a distance sensing probe), the memory 1110 may contain suitable instructions for performing a comparison of the received signal to the predetermined distance, and the processor 1120 may be configured to perform the instructions. For example, the indicating device 180 may receive the raw data signal via device interface 1110, the processor 1120 may convert the raw data into a numerical value for the predetermined distance, and the numerical value may be compared to the predetermined distance. If the numerical value is equal to or lower than the predetermined distance, then the processor 1120 may instruct the indicator 1130 to indicate that the predetermined distance has been reached. For example, the indicator 1130 may provide an audio or visual signal to the operator, or may comprise an electronic controller configured to provide a command signal to an electronically controlled motion controller to perform the operation of advancing the needle and expelling the embryo (with the memory 1110 containing suitable instructions for providing control signals to the actuators). The indicating device 180 may also be configured to further indicate to the user when the automatic procedure of advancing the need and expelling the embryo has been completed (for example an audio or visual signal). Alternatively, the indicator 1130 may comprise a display displaying the measured distance alongside the predetermined distance.

In the case of the measurement assembly comprising a camera and the measurement being a qualitative measurement, the indicating device may merely be a display for displaying the real-time image captured by the camera, optionally with a comparison overlay on the display where appropriate. Alternatively, the memory 1110 may store instructions for performing image analysis of the image data to automatically determine if the image indicates that the predetermined distance has been reached. The processor 1120 may be configured to carry out the instructions. The processor 1120 may then instruct the indicator 1130 to indicate that the predetermined distance has been reached. For example, the indicator 1130 may provide an audio or visual signal to the operator, or may provide a command signal to an electronically controlled motion controller to perform the operation of advancing the needle and expelling the embryo.

Whilst FIG. 11 shows the motion controller and the indicating device as separate devices, indicating device and motion controller may be incorporated into a single device. Further, the measurement assembly may instead be connected to the indicating device indirectly via a device interface of the motion controller.

Figure 12:
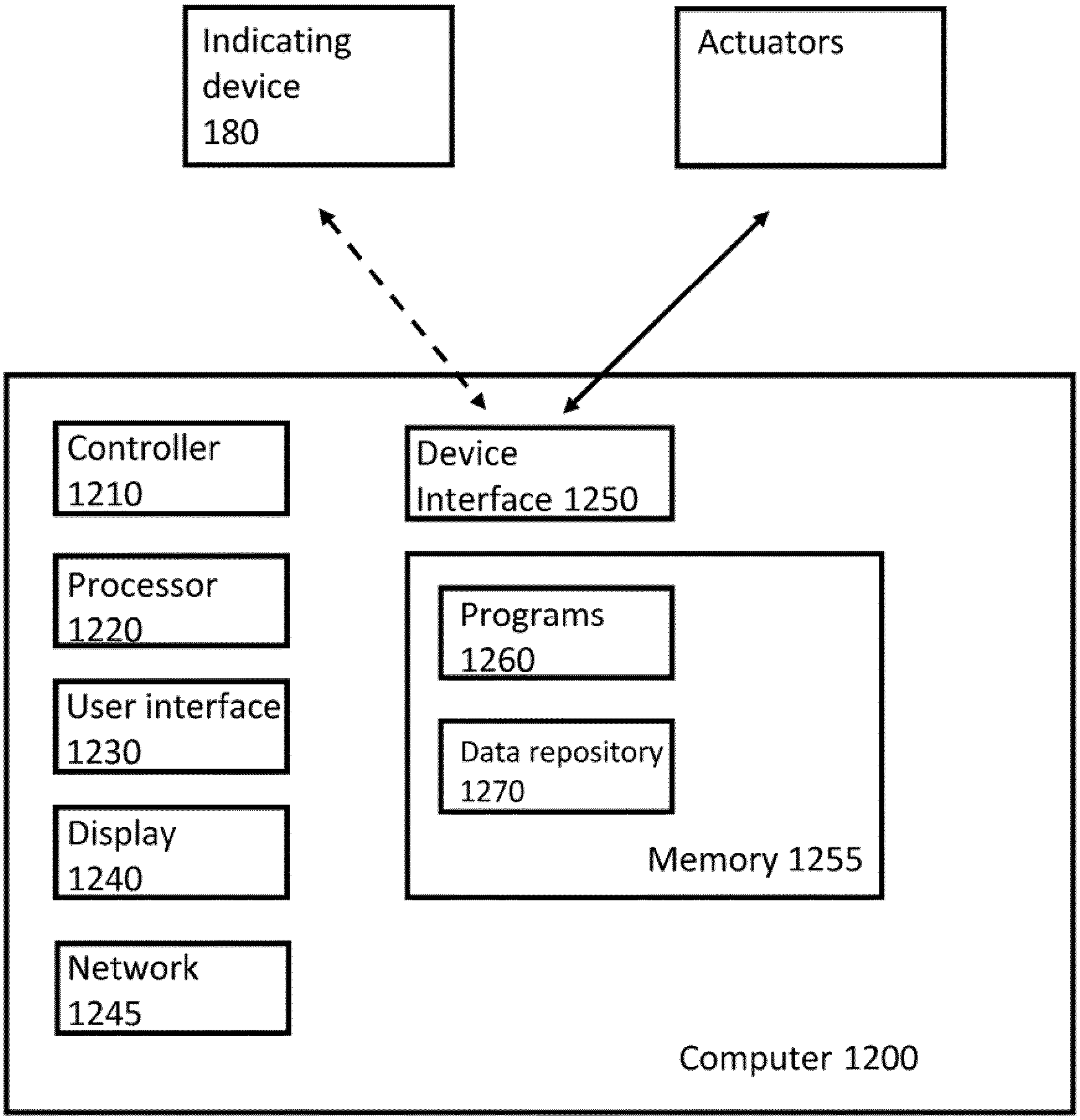
FIG. 12 shows a diagram of a computer that may be used to control the apparatus according to one or more embodiments shown and described herein.

FIG. 12 shows a diagram of a computer 1200 that may be used to control one or more of the actuators disclosed herein. The computer 1200 may comprise one or more of a controller 1210, a processor 1220, a user interface 1230, a display 1240, a network connection 1245, a device interface 1250, and a memory 1255 storing instructions for programs 1260 and a data repository 1270. It will be appreciated than any suitable computing system may be used for the computer 1200 and that the device shown in FIG. 12 is one of many devices that could be used. For example, a distributed computer system may be used, for example comprising one or more servers or client computing systems, using any known distributed computing technique. In some examples, a general-purpose computer or any other processing system may be used to implement the methods disclosed herein. Furthermore, the steps disclosed below may be implemented in software, hardware, or any combination of these to achieve the same steps.

It will be appreciated by the skilled person that the indicating device of FIG. 12 may be powered by any suitable powering means. The memory 1255 may comprise one or more volatile or non-volatile memory devices, such as DRAM, SRAM, flash memory, read-only memory, ferroelectric RAM, hard disk drives, floppy disks, magnetic tape, optical discs, or similar. Likewise, the processor 1220 may comprise one or more processing units, such as a microprocessor, GPU, CPU, multi-core processor or similar. The device interface 1250 may comprise wired connections, such as optic, fiber-optic, ethernet or similar, or any suitable wireless communication.

The device interface 1250 is configured to communicate with (i.e. send and receive control information) one or more electronically controlled actuators. Any of the actuators disclosed herein may be electronically controlled. The device interface 1250 may also be configured to communicate with the indicating device 180. Alternatively, the computer 1200 may comprise all of the features of the indicating device shown in FIG. 11 and may itself be considered as the indicating device 180.

The computer 1200 provides manual control of the electronically controlled actuators by a user of the apparatus. For example, the memory 1255 may comprise instructions for a program 1260 which when executed by processor 1220 causes a graphical user interface (GUI) to be displayed on display 1240, or remotely via network connection 1245. The GUI may comprise appropriate inputs to enable the user to actuate one or more of the actuators. For example, the user may select a function from the GUI, which causes the controller 1210 to send a corresponding control signal to one or more actuators to perform the function.

For example, the user may be able to select a command from the GUI for advancing the body by a certain distance, or at a certain constant speed. The user may be able to select one or more commands for steering the steering mechanism. The user may be able to select one or more commands for advancing the inner body and/or plunger. The commands may correspond to a sequence of commands such that several commands are performed in sequence. For example, the memory 1255 may store instructions for advancing the body 110 until the predetermined distance is reached (i.e. until the indicating device indicates that the predetermined distance is reached), and for subsequently advancing the inner body and plunger to expel the embryo. It may be that all actuators are actuated via such an automated process, or that only some are actuated automatically and the rest are actuated manually (i.e. by user control via the GUI).

The computer 1200 may be configured to receive data from the measurement assembly, either directly or via indicating device 180, and display the data on the GUI alongside the command options. For example, the display 1240 may display real-time image data received from the measurement assembly. The GUI may also display an indication that the predetermined distance has been reached to the user.

In some embodiments, the apparatus may further comprise a motion controller configured to connect to a proximal portion of the body 100, wherein the controller is configured to actuate the first actuator, second actuator, and/or a fourth actuator for advancing the body relative to the motion controller. Any suitable motion controller may be used. For example, the motion controller may comprise one or more linear or rotary mechanisms for actuating the first actuator, the second actuator and/or the fourth actuator. In some embodiments, one or more of the first, second and fourth actuator may comprise a lead screw, each lead screw rotatable to advance the body 110, inner body 160 or plunger 165, the motion controller may be configured to actuate the one or more lead screws. The motion controller may be manually controlled or electronically controlled. The motion controller may be configured to connect to the body via a connector.

Figure 13A:
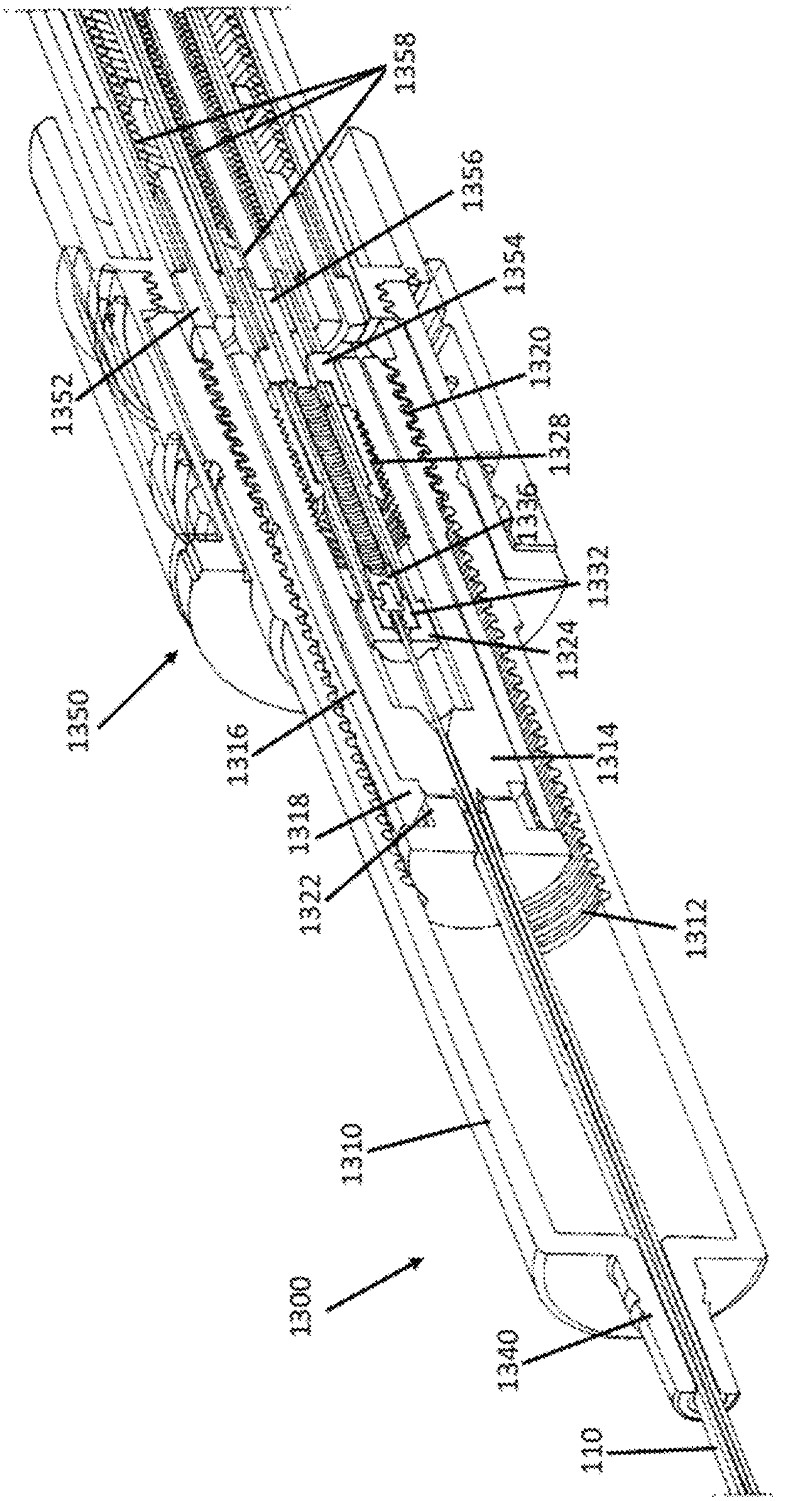
FIG. 13A shows a cross-sectional perspective view of a connector according to one or more embodiments shown and described herein.

FIG. 13A shows a cross-sectional perspective view of a connector 1300 configured to connect to a motion controller 1350. FIG. 13E shows an exploded view of the connector 1300. The connector 1300 comprises a connector housing 1310 which is insertable into a distal end of the motion controller 1350. The connector 1300 also comprises a body connector 1314 fixedly receiving a proximal portion of the body 110 (e.g. by a frictional fit or by adhesive), an inner body connector 1324 fixedly receiving a proximal portion of the inner body 160 (e.g. by frictional fit or by adhesive) and a plunger connector 1332 fixedly receiving a proximal portion of the plunger 165 (e.g. by frictional fit or by adhesive).

The body connector 1314 is received by the connector housing 1310 and is slidable relative to the connector housing 1310 at a fixed rotational orientation. For example, the connector housing 1310 may comprise a longitudinally extending protrusion or recess and the body connector 1314 may comprise a corresponding recess or protrusion such that the body connector 1314 is only receivable in the connector housing 1310 at a single rotational orientation. The connector 1300 further comprises a body lead screw 1316 having an external screw thread 1320 which corresponds to an internal screw thread 1312 of the connector housing 1310. The body lead screw 1316 abuts the body connector 1314 such that, when turning the body lead screw 1316 to advance the body lead screw distally, the body connector 1314 also advances distally (but in a fixed orientation). In the illustrated embodiment, the body lead screw 1316 is connected to the body connector 1314 by one or more protrusions 1318 which are received by a corresponding recess 1322 in the body connector. The interaction between the protrusion 1318 and the recess 1322 means that the body lead screw 1316 abuts the body connector 1314 when it slides both distally and proximally, meaning the body lead screw 1316 is able to both advance and retract the body connector 1314 and thus the body 110. In some embodiments the protrusion 1318 may instead be located on the body connector 1314 and the recess on the body lead screw 1316.

The inner body connector 1324 is housed by the body connector 1314 and is slidable relative to the connector housing 1310 and the body connector 1314. In some embodiments, the inner body connector 1324 may be slidable relative to the connector housing 1310 and body connector 1314 at a fixed rotational orientation (for example using corresponding protrusions and recessions in the body connector 1314 and the inner body connector 1324 as previously disclosed).

Figure 13B:
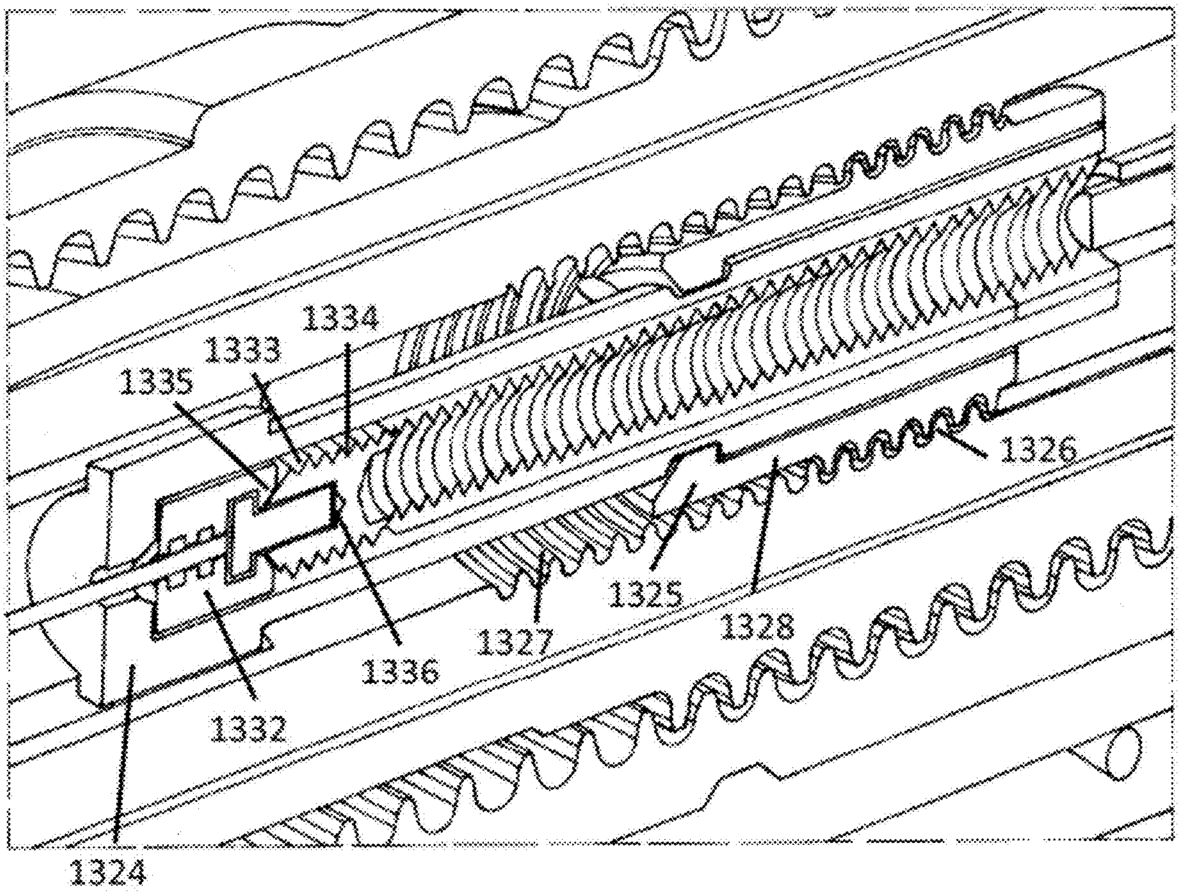
FIG. 13B shows a close-up view of a part of the connector shown in FIG. 13A.

FIG. 13B shows a close up of the inner body connector 1324 and the plunger connector 1332 shown in FIG. 13A. The connector further comprises an inner body lead screw 1328 having an external screw thread 1326 which corresponds to an internal screw thread 1327 of the body connector 1314. The inner body lead screw 1328 abuts the inner body connector 1324 such that, when turning the inner body lead screw 1328 to advance the inner body lead screw 1328 distally, the inner body connector 1324 also advances distally. In the illustrated embodiment, the inner body lead screw 1328 is connected to the inner body connector 1324 by one or more protrusions 1325 which are received by a corresponding recess in the inner body connector 1325. The interaction between the protrusion 1325 and the recess means that the inner body lead screw 1328 abuts the inner body connector 1324 when it slides both distally and proximally, meaning the inner body lead screw 1328 is able to both advance and retract the inner body connector 1324 and thus the inner body 160. In some embodiments the protrusion 1325 may instead be located on the inner body connector 1324 and the recess on the inner body lead screw 1328. In some embodiments, the inner body connector 1324 and inner body lead screw 1328 may be a single unitary body.

The plunger connector 1332 is housed by the inner body connector 1324 and is slidable relative to the connector housing 1310, the body connector 1314 and the inner body connector 1324. In some embodiments, the plunger connector 1332 may be slidable relative to the connector housing 1310, body connector 1314 and inner body connector 1324 at a fixed rotational orientation (for example using corresponding protrusions and recessions in the inner body connector 1324 and the plunger connector 1332 as previously disclosed). The connector further comprises a plunger lead screw 1336 having an external screw thread 1333 which corresponds to an internal screw thread 1334 of the inner body connector 1324. The plunger lead screw 1336 abuts the plunger connector 1332 such that, when turning the plunger lead screw 1336 to advance the plunger lead screw 1336 distally, the plunger connector 1332 also advances distally. In the illustrated embodiment, the plunger lead screw 1336 is connected to the plunger connector 1332 by one or more protrusions 1335 in the plunger connector 1332 which are received by a corresponding recess in the plunger lead screw 1336. The interaction between the protrusion 1335 and the recess means that the plunger lead screw 1336 abuts the plunger connector 1332 when it slides both distally and proximally, meaning the plunger lead screw 1336 is able to both advance and retract the plunger connector 1332 and thus the plunger 165. In some embodiments the protrusion 1335 may instead be located on the plunger lead screw 1336 and the recess on the plunger connector 1332. In some embodiments, the plunger connector 1332 and plunger lead screw 1336 may be a single unitary body.

The connector 1300 may comprises an interlocking feature 1340 at a distal end, such as a Luer lock, for securing the distal end of the connector 1300 to the next distal component of the apparatus. For example, the interlocking feature 1340 may be configured to interlock with a corresponding interlocking feature on the balloon catheter disclosed below, and as show in FIG. 14J, or it may be configured to interlocking with a proximal end of the steering mechanism disclosed above, such as handle 970.

Figure 13C:
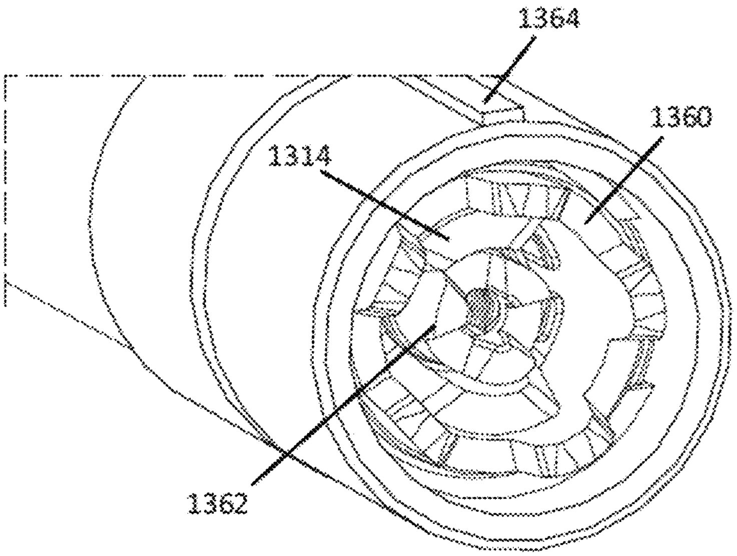
FIG. 13C shows a perspective view of a proximal end of a connector according to one or more embodiments shown and described herein.
Figure 13D:
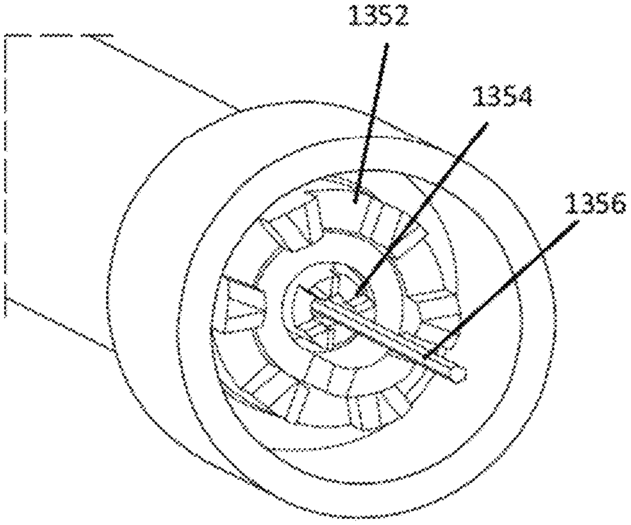
FIG. 13D shows a perspective view of a distal end of a motion controller according to one or more embodiments shown and described herein.
Figure 13E:
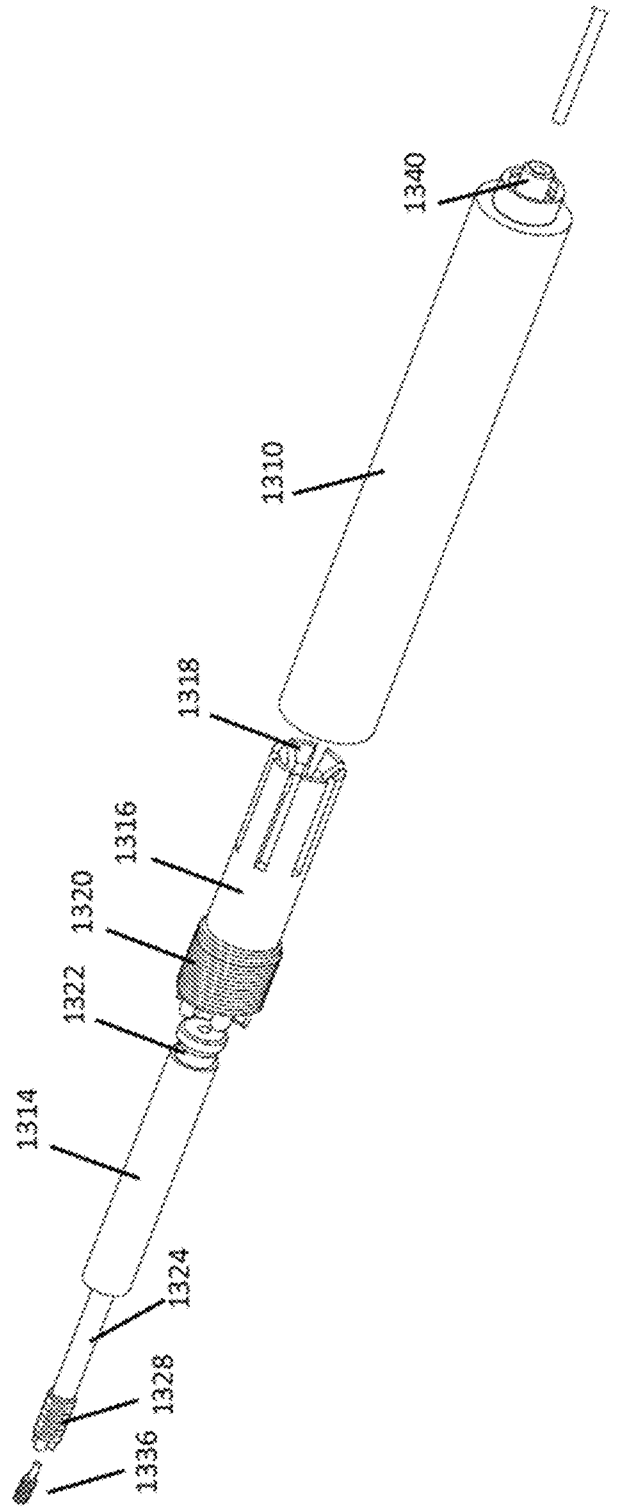
FIG. 13E shows an exploded view of the connector shown in FIG. 13A.

FIG. 13C shows a perspective view of a proximal end of the connector 1300. FIG. 13D shows a perspective view of a distal end of the motion controller 1350. The proximal end of the connector 1300 is configured to connect with the distal end of the motion controller 1350. The body lead screw 1316 comprises a toothed proximal end 1360 configured to engage with a body lead screw driver 1352 of the motion controller 1350. The inner body lead screw 1328 comprises a toothed proximal end 1362 which is configured to engage with an inner body lead screw driver 1354 of the motion controller 1350. The plunger lead screw comprises a toothed proximal end (not shown) configured to engage with a plunger lead screw driver 1356 of the motion controller 1350. The proximal end of the connector housing 1310 may further comprise a locking feature such as a protrusion 1364 configured to be received by a recess of the distal end of the motion controller (not shown) in order to prevent relative rotation of the distal end of the motion controller 1350 and connector housing 1310. The connector 1300 may be connected to the motion controller 1350 by a push-fit, click-fit, frictional-fit, or similar mechanism. The lead screw drivers 1352, 1354 and 1356 may be distally biased by springs 1358 (see FIG. 13A) in order to ensure engagement with the proximal ends of the lead screws during rotation.

Whilst the illustrated embodiment illustrates a connector which actuates the body connector, inner body connector and plunger connector by the lead screw mechanisms, it will be appreciated that in other embodiments the connector only actuates one or more of the body connector, inner body connector and plunger connector by a lead screw mechanism. For example, the connector may comprise only the body connector 1314, actuated by the body lead screw 1316 as described above, and the needle and plunger may be actuated differently (i.e. by a linear motion mechanism). It will also be appreciated that the outermost screw thread of a given embodiment engages the inner screw thread 1312 of the connector housing 1310. For example, in embodiments where the connector 1300 actuates only the inner body 160 and plunger 165 by the screw thread mechanisms disclosed, the outer thread 1326 of the inner body lead screw 1328 engages with the inner thread 1312 of the connector housing 1310, rather than the inner screw thread of the body connector 1314.

The connector housing 1310, connectors 1314, 1324 and 1332 and lead screws 1316, 1328 and 1336 may be made of any suitable material such as plastic and may be molded or 3D printed. Likewise, the lead screw drivers 1352, 1354 and 1356 may be made of any suitable material such as plastic.

Electrical wiring and/or optical fibers extending from the measurement portion 170 through the body 110 from the distal end of the apparatus may terminate at the connector 1300. In particular, a proximal portion of electrical wiring extending from the distal end of the apparatus through the body 110 may be electrically connected to an electrical terminal of the connector. The motion controller may comprise a corresponding electrical terminal biased towards the electrical terminal of the connector to maintain contact with the electrical terminal of the connector. Similarly, a proximal portion of the optical fibers may be optically connected to an optical terminal of the connector 1300, and the motion controller may comprise an optical terminal configured to form a face seal with the optical terminal of the connector 1300 and biased towards the optical terminal of the connector 1300 to maintain the face seal with the first optical terminal.

Figure 13F:
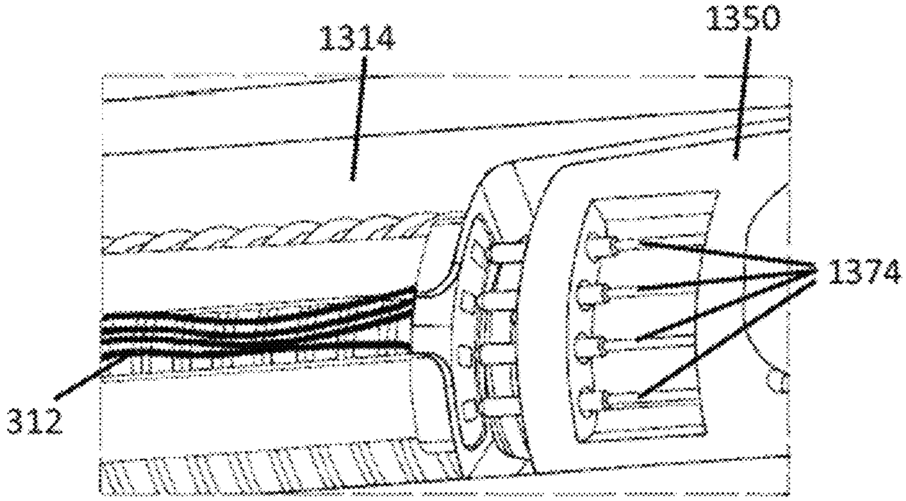
FIG. 13F shows a perspective view of a connection between a body connector and a distal end of a motion controller according to one or more embodiments shown and described herein.

FIG. 13F shows a perspective view of the connection between the body connector 1314 and the distal end of the motion controller 1350. The illustrated embodiment shows a proximal portion of electrical cables 312 (see e.g. FIG. 3) which extend from the measurement portion (e.g. camera 310), through the body 110 to the connector 1300. The cables 312 are electrically connected to an electrical terminal (such as a printed circuit board) on the body connector 1314 (e.g. by soldering). The electrical terminal comprises electrical connections which are configured to engage electrical pins 1374 on the motion controller 1350. The electrical pins 1374 are biased distally such that the electrical connection between the pins 1374 and the electrical terminal of the body connector 1314 is maintained as the body connector 1314 is advanced through the connector housing 1300. It will be appreciated that optical connections between the connector 1300 and the motion controller 1350 can be similarly established and maintained.

Figure 13G:
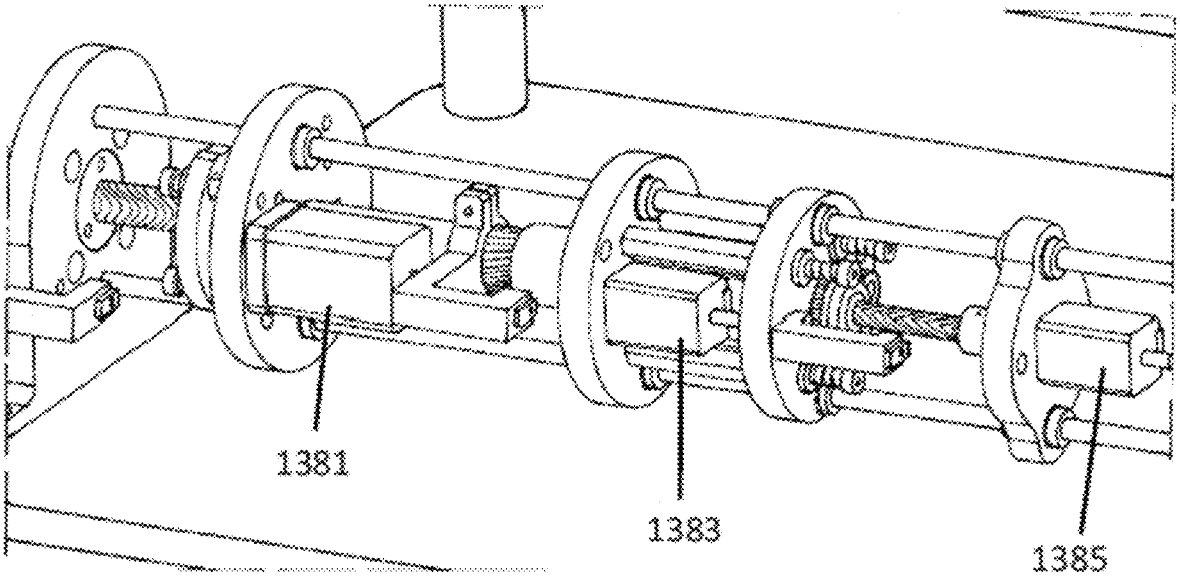
FIG. 13G shows a perspective view of a proximal portion of a motion controller according to one or more embodiments shown and described herein.

FIG. 13G shows a perspective view of a proximal portion of the motion controller 1350. The motion controller 1350 comprises a first motor 1381, a second motor 1383 and a third motor 1385. In one embodiment, the first motor 1381 may be configured to drive the body lead screw driver 1352, the second motor 1383 may be configured to drive the inner body lead screw driver 1354 and the third motor may be configured to drive the plunger lead screw driver 1356. The motion controller 1350 may be configured to advance/retract the body 110, inner body 160 and plunger 165 at the same rate by running the first, second and third motors 1381, 1383, 1385 in unison at the rate corresponding to the same advancement speed of the body 110, inner body 160 and plunger 165. The motion controller 1350 may also be configured to advance/retract the inner body 160 and plunger 165 at the same rate relative to the body 110 by running the second and third motors 1383, 1385 in unison at the rate corresponding to the same advancement speed of the inner body 160 and plunger 165. The motion controller 1350 may also be configured to advance/retract the plunger 165 relative to the inner body 160 by running the third motor 1385 alone.

Alternatively, the first motor 1381 may be configured to turn each of the lead screw drivers 1352, 1354 and 1356 (e.g. via a first threaded rod) to advance the lead screws 1316, 1328 and 1336 at the same rate (to advance the body 110, the inner body 160 and the plunger 165 at the same rate). The second motor 1383 may be configured to turn the inner body lead screw driver 1354 and the plunger lead screw driver 1356 (e.g. via a second threaded rod) to advance the inner body lead screw 1328 and the plunger lead screw 1336 at the same rate (to advance the inner body 160 and plunger 165 at the same rate). The third motor 1386 may be configured to turn the plunger lead screw driver 1356 (e.g. via a threaded rod) to advance the plunger 165.

The motion controller 1350 may further comprise an axial motor (not shown) to retract the plunger lead screw driver 1352 before connection or disconnection of the connector 1300, in order to prevent damage to the plunger lead screw driver 1352 during connection or disconnection of the connector 1300.

The connector 1300 may be assembled in the following steps (the steps need not necessarily be performed in chronologically in the order presented). The proximal portion of the plunger 165 may be fixed to the plunger connector 1332. The plunger connector 1332 may be connected to the plunger lead screw 1336 (for example the connector and lead screw are pushed together until the protrusion falls into the recess to secure the connector and lead screw together). The proximal portion of the inner body 160 may be connected to the inner body connector 1324. The inner body connector 1324 may be connected to the inner body lead screw 1328 (e.g. by pushing the connector and lead screw are together until the protrusion falls into the recess to secure the connector and lead screw together). The proximal portion of the body 110 may be connected to the body connector 1314. The body connector 1314 may be connected to the body lead screw 1316 (e.g. by pushing the connector and lead screw are together until the protrusion falls into the recess to secure the connector and lead screw together). The distal end of the plunger 165 may be passed through the inner body connector 1324 from the proximal end and through the inner body 160. The plunger lead screw 1336 may be screwed to the inner body connector 1324. The distal end of the inner body 160 may be passed through the body connector 1314 from the proximal end and through the body 110. The inner body lead screw 1328 may be screwed to the body connector 1314. The distal end of the body may be passed through the connector housing 1310 from the proximal end. The body lead screw 1316 may be screwed to the connector housing 1310. The lead screws may then be actuated to moved the body 110, inner body 160 and plunger 165 to the correct relative positions.

When the connector 1300 is assembled, the plunger lead screw 1336 may be actuated to aspirate the fluid containing the embryo. The connector 1300 is then connected to the motion controller 1350.

The length from the proximal end of the body connector 1314 to the distal tip of the body 110 may be about 300 mm to 400 mm, preferably 325 mm to 375 mm, for example 358 mm. The maximum length of the connector 1300 from the proximal end to the distal tip of the body 110 may be bout 400 mm to 500 mm, preferably 425 mm to 475 mm, for example 450 mm.

Figure 13H:
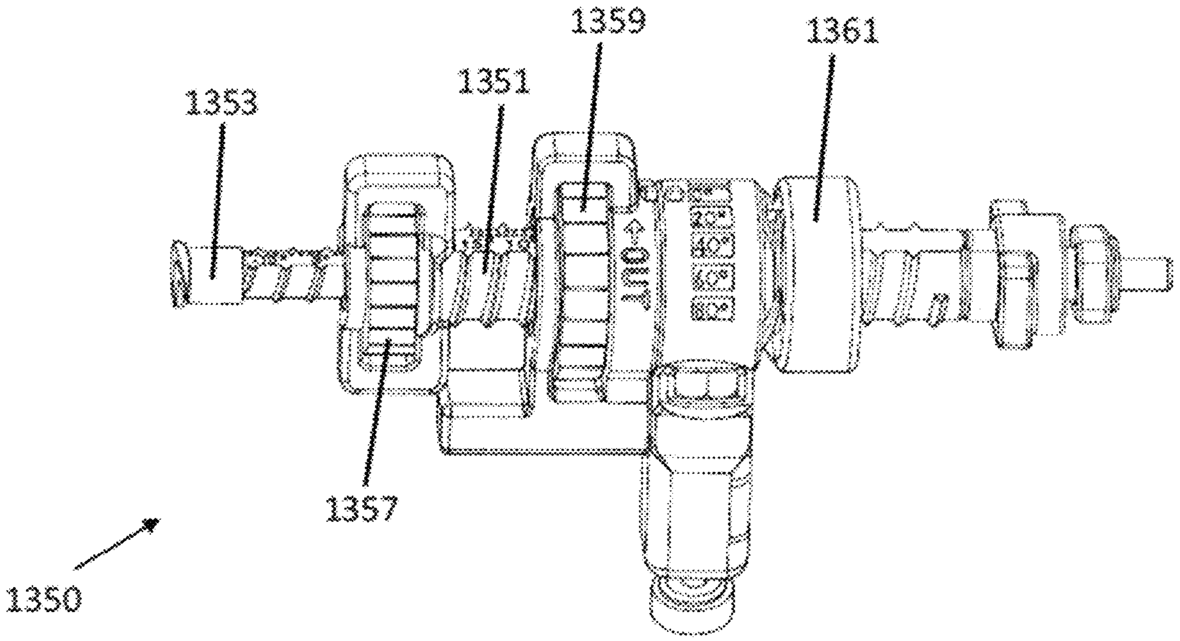
FIG. 13H shows a perspective view of a motion controller according to one or more embodiments shown and described herein.

FIG. 13H shows a perspective view of a motion controller 1350 according to an embodiment. The motion controller 1350 is configured to connect to a proximal portion of the body 110 and to actuate on said body 110. In the embodiment shown in FIG. 13H, the motion controller 1350 comprises two lead screws 1351, 1353 configured to advance/retract the body 110, and to rotate and advance/retract an outer catheter which houses the body 110 in an embodiment. In the embodiment shown the motion controller 1350 further comprises three actuation mechanisms 1357, 1359, 1361, each actuation mechanism configured to actuate on one of the lead screws 1351, 1353. The actuation of the lead screws 1351, 1353 may be manual or may be motorized. Although in this embodiment two lead screws 1351, 1353 are shown, in other embodiments there may be only one lead screw, depending on the elements intended to be moved by the motion controller 1350. The motion controller 1350 allows fine and precise control of the movement of the body 110 and of the outer catheter housing the body, as well as fixing the outer catheter in the required position. In an embodiment, the motion controller 1350 may be actuated based on a real time image obtained by an imaging device, such as a camera, present in the apparatus 100.

In some embodiments, the apparatus may further comprise an outer balloon catheter.

Figure 14A:
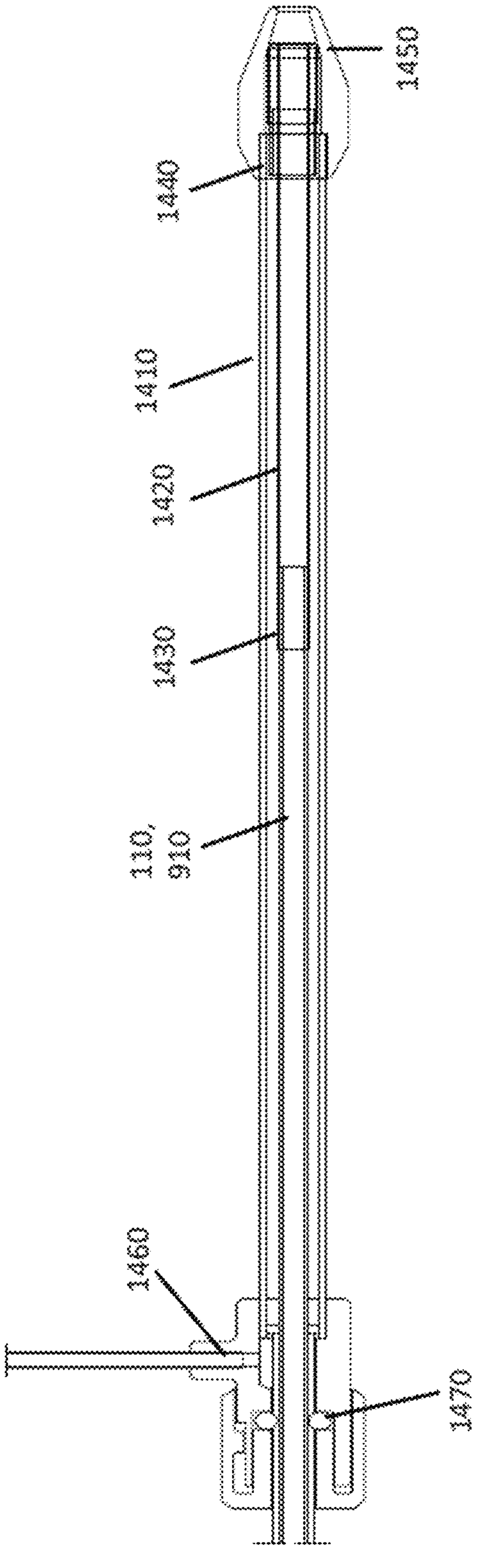
FIG. 14A shows a cross-sectional side view of a balloon catheter according to one or more embodiments shown and described herein.

FIG. 14A shows a cross-sectional side view of a balloon catheter according to one or more embodiments. The balloon catheter comprises an outer tubular body 1410 which slidably receives an evertable tube 1420. The evertable tube is configured to receive the body 110 or tube wall 910 of the steering mechanism. In the illustrated embodiment, the evertable tube 1420 is attached to the body 110 or tube wall 910 to form a first seal 1430 at one end of the evertable tube 1420. The evertable tube is attached to the inner surface of the outer tubular body to form a second seal 1440 at another end of the evertable tube. At a proximal end of the balloon catheter, the body 110 or tube wall 910 enters the balloon catheter through a slidable seal 1470 formed by, for example, an O-ring, which allows the body 110 or tube wall 910 to advance through the balloon catheter whilst fluidically sealing the proximal end of the balloon catheter from the interior. The balloon catheter is configured to contain a fluid (e.g. water) in the volume formed between the evertable tube 1420 and the outer tubular body 1410 (wherein the volume is fluidically sealed by the seals 1470, 1430 and 1440). The balloon catheter may also comprise a port 1460 for filling the said volume, for example fluidically connected to a reservoir.

Figure 14B:
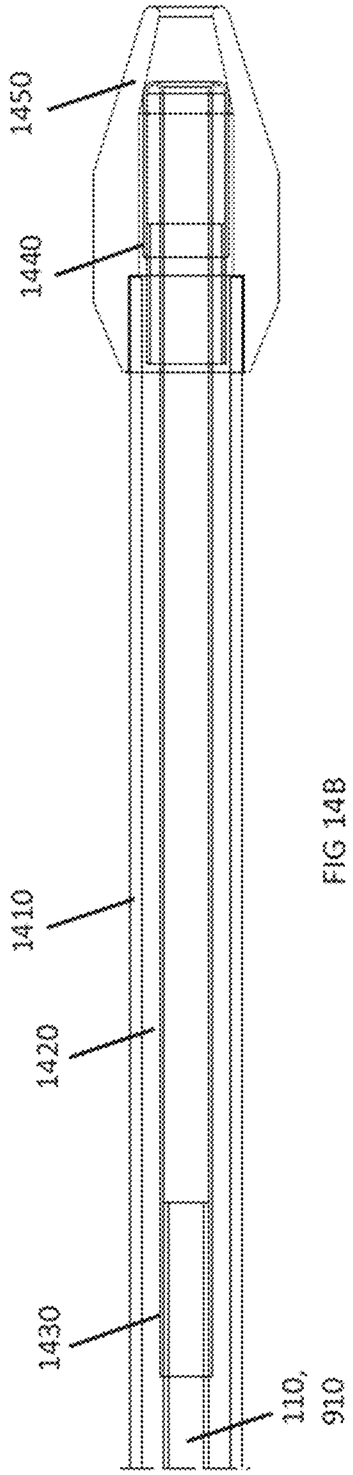
FIGS. 14B and 14C show close-up cross-sectional side views of the balloon catheter of FIG. 14A.

FIG. 14B shows a close-up cross-sectional side view of the balloon catheter of FIG. 14A in a non-everted state. In use, the tip 1450 of the outer tubular body may be placed at the entrance of the cervix of a patient. The body 110 or tube wall 910 may then be advanced through the balloon catheter. The forward pressure of the body 110 or tube wall 910 and the fluid pressure causes the evertable tube 1420 to evert in the distal direction (i.e. through the cervix). The evertable tube 1420 acts as a roller as it everts through the cervix, and the fluid between the evertable tube 1420 and the outer tubular body 1410 limits shear forces, thereby faciliting insertion of the body 110 or tube wall 910 into the uterus.

Figure 14C:
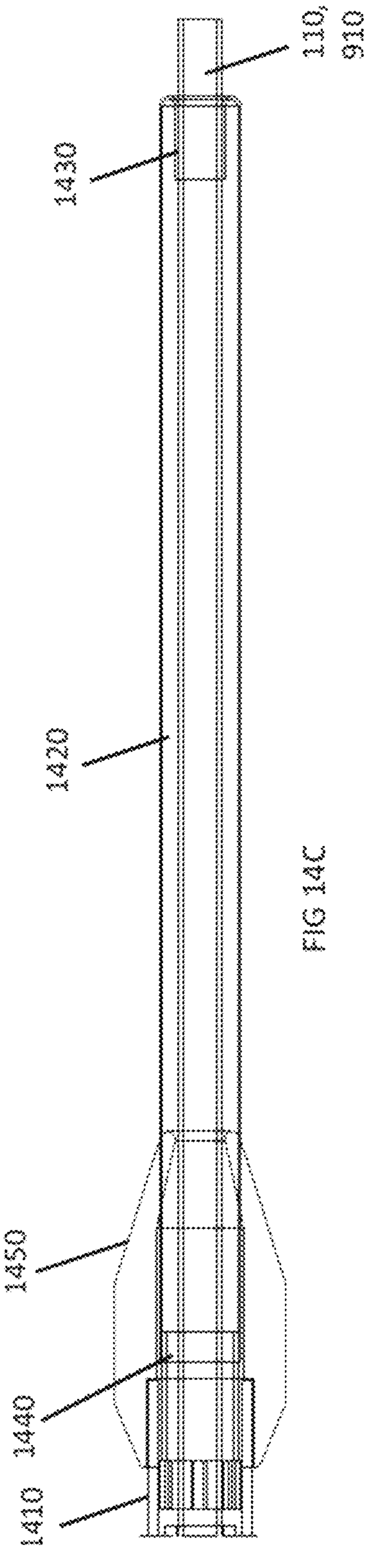

FIG. 14C shows a close-up cross-sectional side view of the balloon catheter of FIG. 14A in a fully everted state. As can be seen, body 110 or tube wall 910 may be advanced through the balloon catheter to a maximal position defined by the most distal position of the seal 1430 (after which the tube 1420 is not able to evert further). The seal 1430 may be positioned on body 110 or the tube wall 910 such that it protrudes from the tube 1420 by a predetermined distance.

Figure 14D:
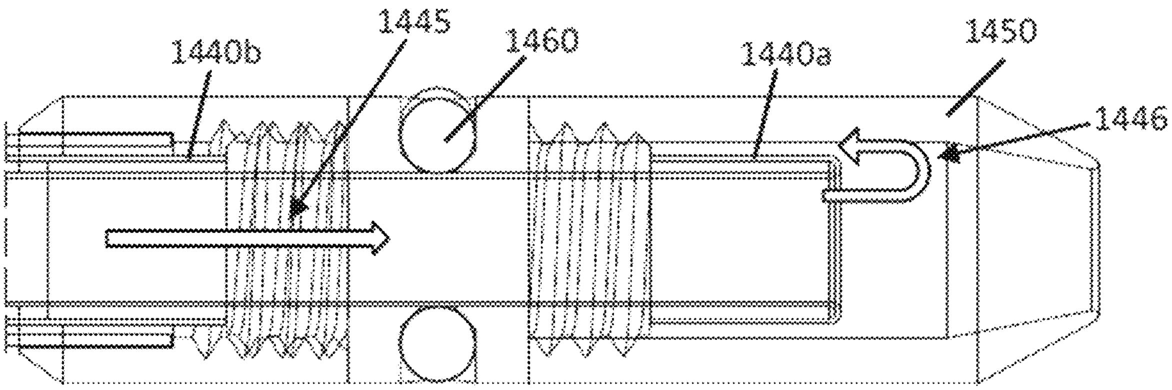
FIG. 14D shows a cross-sectional side view of another balloon catheter according to one or more embodiments shown and described herein.
Figure 14E:
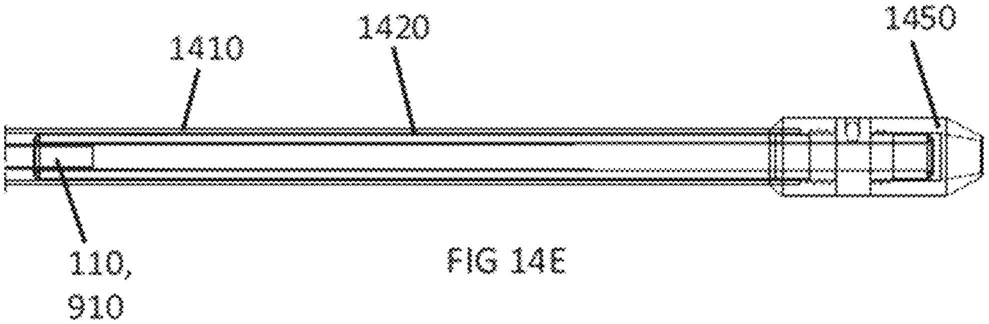
FIG. 14E shows a cross-sectional side view of the balloon catheter of FIG. 14D in a non-everted state.
Figure 14F:
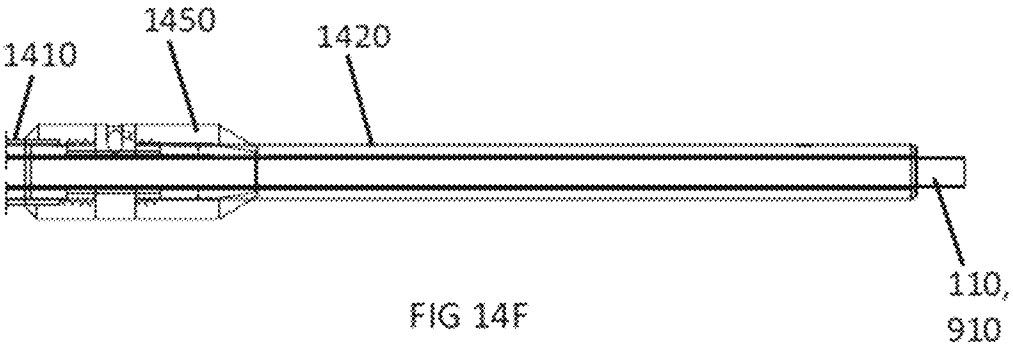
FIG. 14F shows a cross-sectional side view of the balloon catheter of FIG. 14D in an everted state.

FIG. 14D shows a cross-sectional side view of another balloon catheter according to one or more embodiments. Unlike the embodiment shown in FIGS. 14A to 14C, the evertable tube 1420 is fully rolled back on itself and is attached to the tip 1450 to form two seals 1440*a* and 1440*b* on the outer tubular body. The evertable tube 1420 is configured to receive the tube wall 910 or the body 110, for example by a frictional fit or may adhesive. The inner volume of the evertable tube may be pre-filled with fluid or the balloon catheter may comprise a port 1460 for filling the evertable tube with fluid. As in the previous embodiment, as the tube wall 910 or the body 110 is advanced, the inner part of the evertable tube 1420 travels forward (distally, see arrow 1445) which creates forces on the leading distal edge of the tube 1420 (indicated by arrow 1446). Accordingly, the tube 1420 everts as the tube wall 910 or body 110 is advanced through the balloon catheter. FIG. 14E shows a cross-sectional side view of the balloon catheter of FIG. 14D in a non-everted state, and FIG. 14F shows a cross-sectional side view of the balloon catheter of FIG. 14D in an everted state.

Figure 14G:
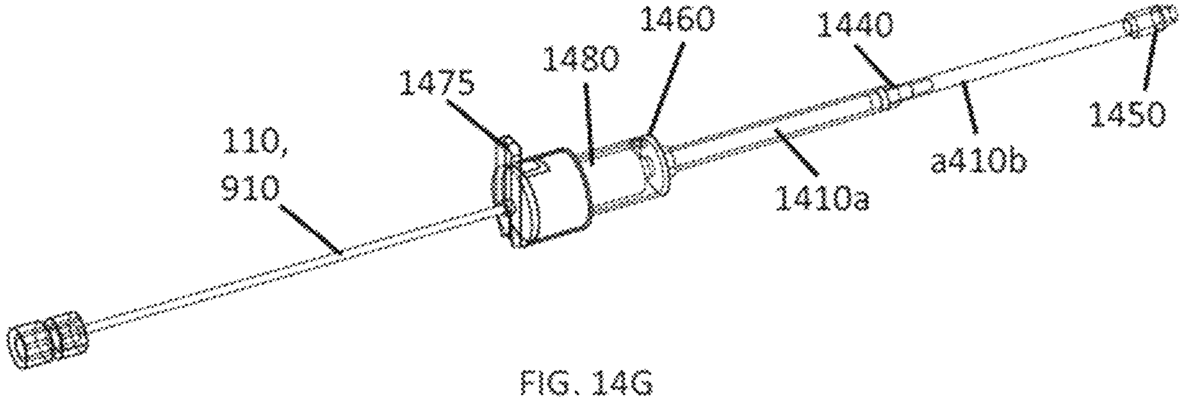
FIG. 14G shows a perspective view of another balloon catheter according to one or more embodiments shown and described herein.

FIG. 14G shows a perspective view of another balloon catheter according to one or more embodiments. The balloon catheter comprises an outer tubular body formed by proximal section 1410*a*, distal section 1410*b* and tip 1450. As in the other embodiments, the balloon catheter further comprises an evertable tube 1420 slidably received in the outer tubular body and configured to receive the tube wall 910 or the body 110. The balloon catheter further comprises a reservoir of fluid 1480, and a port 1460 (e.g. a valve) for filling the reservoir 1480 with fluid.

Figure 14H:
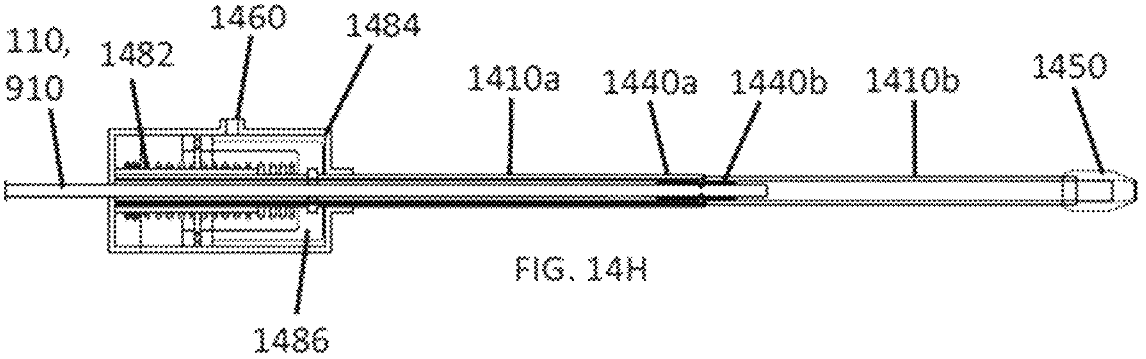
FIG. 14H shows a cross-sectional side view of the balloon catheter shown in FIG. 14G.

FIG. 14H shows a cross-sectional side view of the balloon catheter shown in FIG. 14G. The reservoir 1480 comprises a piston housing 1484, a piston 1486 and a biasing mechanism (e.g. a spring) configured to bias the piston distally. The biasing mechanism 1482 causes the fluid in the reservoir to be pressurised.

Figure 14I:
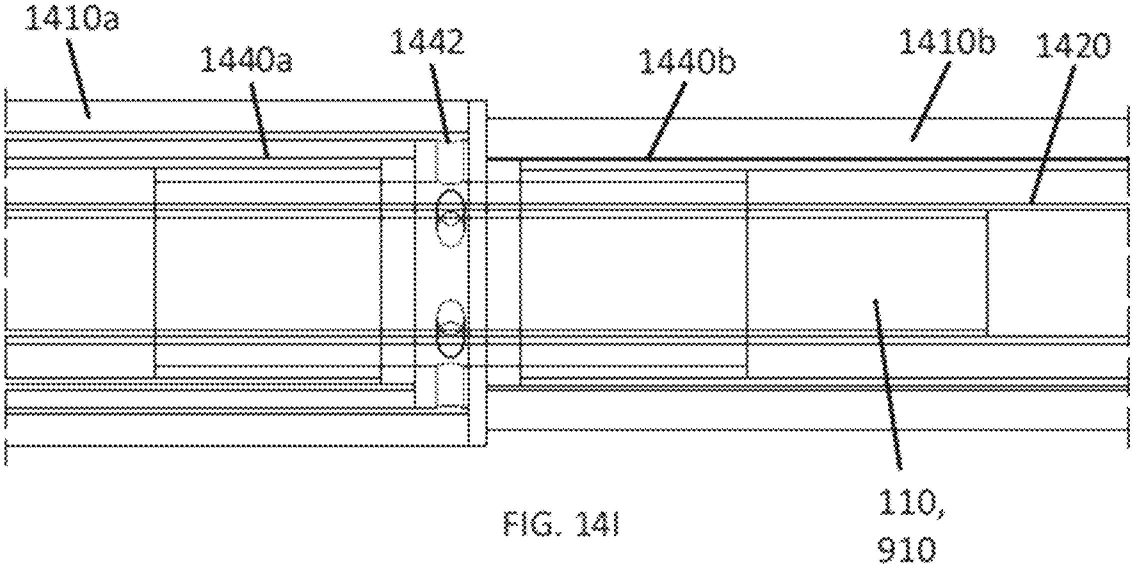
FIG. 14I shows another cross-sectional side view of the balloon catheter shown in FIG. 14G.

FIG. 14I shows another cross-sectional side view of the balloon catheter shown in FIG. 14G. The evertable tube is fully rolled back on itself and is attached to the outer tubular body to form two seals 1440*a* and 1440*b* on the outer tubular body. A port 1442 between the seals 1440*a* and 1440*b* fluidically connects the interior of the evertable tube 1420 with the fluid in the reservoir 1480 (via a fluid path extending along the interior of the proximal section 1410*a* and into the reservoir). Accordingly, the pressurised fluid in the reservoir 1480 serves to pressurise the evertable tube 1420 such that it does not deflate.

Figure 14J:
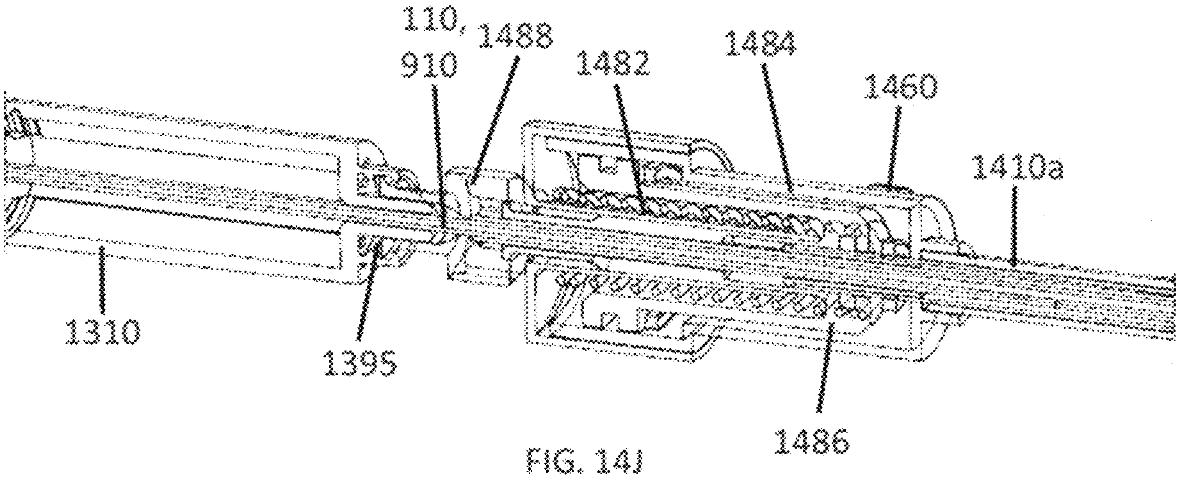
FIG. 14J shows a perspective view of another balloon catheter according to one or more embodiments shown and described herein.

The balloon catheter may further comprise a releasable locking mechanism for locking the piston in a proximal position. For example, there may be provided a tab 1475 (see FIG. 14G) which is configured to prevent the piston from moving distally when located between an external flange 1488 and a proximal end of the reservoir 1480 (see FIG. 14J). When the tab is removed, the external flange 1488 (and therefore the piston 1486 may move distally to pressurise the fluid. FIG. 14J shows a perspective cross-sectional view of the balloon catheter when the tab 1475 has been removed.

As shown in FIG. 14J, the piston housing 1484 and piston 1486 may be configured to slidably receive the tube wall 910 or body 110. In particular, the piston housing 1484 and piston 1486 may comprise proximal and distal holes for slidably receiving the tube wall 910 or body 110. The tube wall 910 or body 110 may be fluidically separated from the fluid in the reservoir.

Figure 14K:
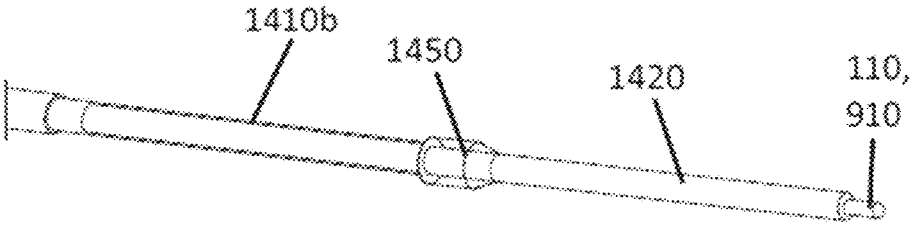
FIG. 14K shows a perspective view of the distal end of the balloon catheter shown in FIG. 14G in an everted state.
Figure 14L:
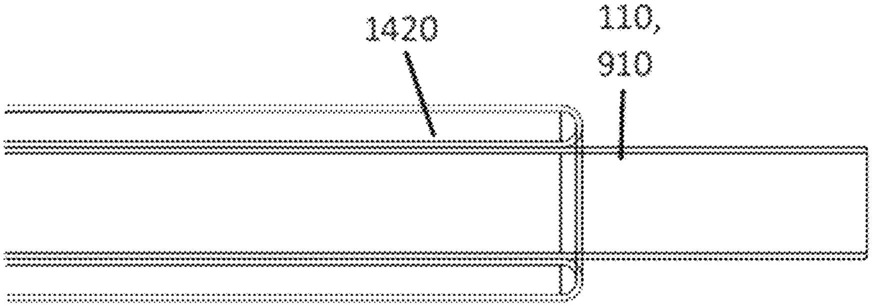
FIG. 14L shows a close up cross-sectional side view of the distal tip of the balloon catheter shown in FIG. 14K.

As in the previous cases, advancing the tube wall 910 or body 110 creates a forward pressure on the inner surface of the evertable tube 1420 (by friction or by the tube wall 910 or body 110 being attached to the evertable tube 1420). FIG. 14K shows a perspective view of the distal end of the balloon catheter shown in FIG. 14G in an everted state. FIG. 14L shows a close up cross-sectional side view of the distal tip of the balloon catheter in the everted state.

The evertable tube may be made of any flexible tubing, for example any suitable thermoplastic elastomer such as polyether block amide. (and the evertable tube may be fixed to the outer tubular body and tube wall 910 or body 110 by any suitable medical adhesive such as any cyanoacrylate adhesive (e.g. a UV curable adhesive).

The outer diameter of the evertable tube in the everted state may be about 1.9 mm to 2.5 mm and preferably 2.1 mm to 2.3 mm, for example 2.2 mm.

Figure 15:
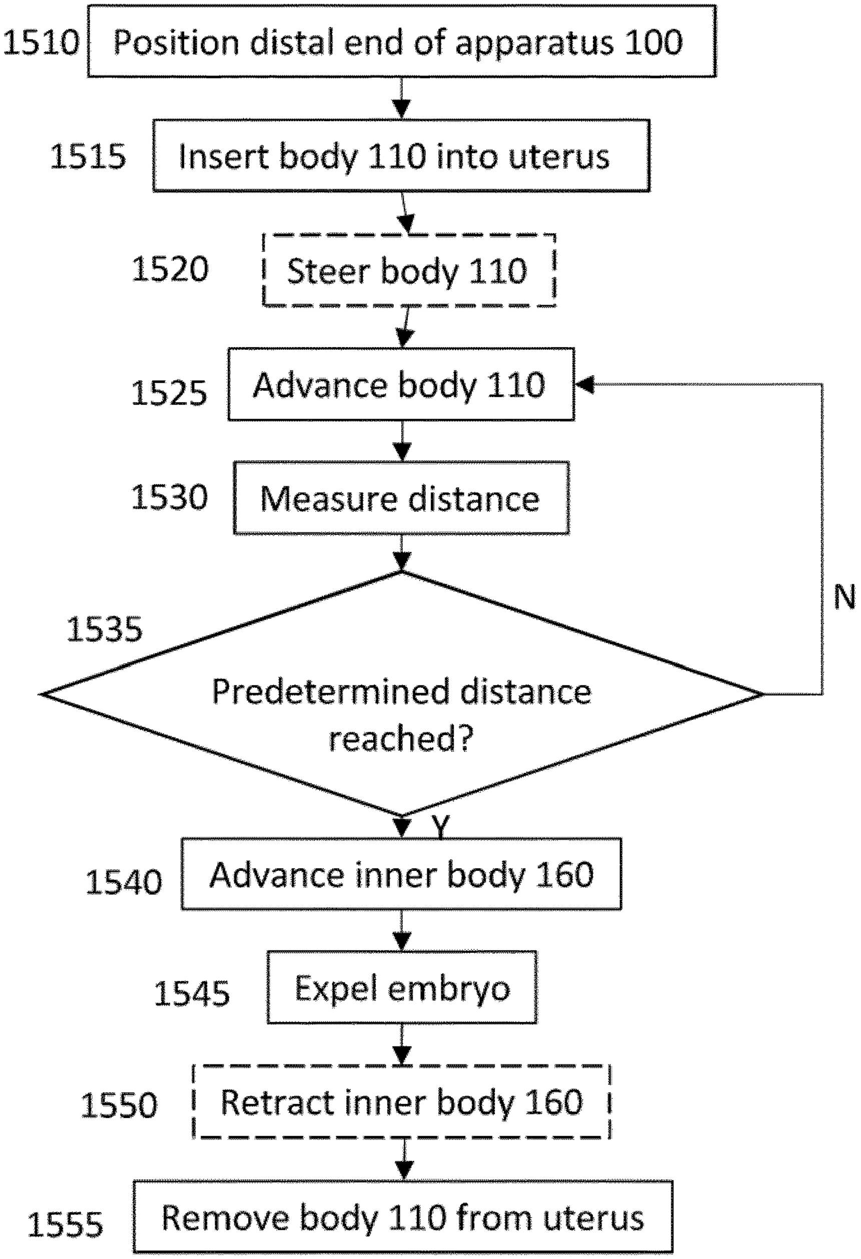
FIG. 15 shows a flow chart of an exemplary method for using a apparatus according to one or more embodiments shown and described herein.

FIG. 15 shows a flow chart of an exemplary method for using the apparatus 100 according to the present disclosure. In a first step 1510, the distal end of apparatus 100 is positioned against the cervix (for example through a speculum).

In a next step 1515, the body 110 (and optionally the steering mechanism) is inserted into the uterus by advancing the apparatus through the cervix. This may be done by the use of any of the balloon catheters as disclosed herein, or the body 110 may be inserted without the use of a balloon catheter.

In a next step 1520, optionally, the body 110 may be steered by a steering mechanism as disclosed herein.

Next, in step 1525, the body 110 may be advanced through the uterus. For example, the body 110 may be advanced manually by the operator, or the body 110 may be advanced by an electronic motion controller as part of an automatic process or in response to a command inputted by the user.

In step 1530, the distance of the distal opening 150 to the endometrial epithelium may be measured. The measurement may be a qualitative measurement determining whether the distal opening 150 is farther from or at or closer to the predetermined distance (for example as viewed by the user via a fiberscope or camera display, or as determined from image analysis by the indicating device). The measurement may be a quantitative measurement determining a distance value and comparing the distance value to the predetermined distance.

If the distance to the endometrial epithelium is still greater than the predetermined distance, then the body 110 is advanced further into the uterus.

If the predetermined distance has been reached (as indicated by the indicating portion), then the body 110 is held in place and the inner body 160 is advanced (step 1540). The inner body 160 may be advanced manually by the user via an actuator, or may be advanced using a motion controller, either as part of an automatic process or in response to a command inputted by the user.

In step 1545, the embryo is expelled. Again, the embryo may be expelled manually by the user via an actuator, or may be expelled using an electronic motion controller (for example by advancing a plunger), either as part of an automatic process or in response to a command inputted by the user.

Optionally, in step 1550, the inner body 160 may be retracted. The inner body 160 may be retracted manually by the user via an actuator, or may be retracted using an electronic motion controller, either as part of an automatic process or in response to a command inputted by the user.

In step 1555, the body 110 is removed from the uterus. The body 110 may be removed manually by the user, or may be removed using an electronic motion controller, either as part of an automatic process or in response to a command inputted by the user.

The following also forms part of the present disclosure.

A steering mechanism configured to steer a distal portion of the body configured to fit within a lumen of the female reproductive system and an actuator for operating the steering mechanism. The body may be part of any apparatus disclosed herein.

The steering mechanism may comprise a plurality of connected rings forming a tube wall configured to at least partially surround a portion of the body; and at least one cable extending longitudinally along the tube wall and attached to a distal end of the tube wall; wherein the actuator is operable to contract and extend at least one cable to steer the distal portion of the body; preferably wherein the steering mechanism comprises a plurality of said cables located at different circumferential positions about the tube wall.

The actuator may comprise: an inner element; an outer shell housing the inner element, each of the at least one cable being fixedly connected to the outer shell at a proximal portion; the inner element being fixedly connected to the tube wall; the outer shell being rotatable relative to the inner element; and optionally, a handle fixed to the inner element through the outer shell.

The inner element may comprise one or more components biased to abut the outer shell.

The body may be configured to be slidable relative to the steering mechanism and actuator.

A balloon catheter comprising: an outer tubular body; and an evertable tube slidably received in the outer tubular body and configured to receive a steering mechanism for steering a body configured to fit within a lumen of the female reproductive system or a body configured to fit within a lumen of the female reproductive system; wherein the balloon catheter is configured to contain a fluid between the outer tubular body and the evertable tube; and when the steering mechanism or body is advanced, the evertable tube everts.

The balloon catheter may comprise a fluid port for filling the balloon catheter with fluid.

The fluid port may be fluidically connected to a reservoir of fluid.

The reservoir may be formed by a piston housing and a piston, and a biasing mechanism configured to bias the piston distally to pressurise the fluid in the reservoir.

The balloon catheter may further comprise a releasable locking mechanism for locking the piston in a proximal position.

The piston housing and piston may be configured to slidably receive the steering mechanism or body.

The maximum volume of the reservoir may be less than an overfilling volume of the balloon catheter.

The steering mechanism or body may be fixed to the tubular balloon such that the steering mechanism or body is advanceable to a maximum position.

A connector having a connector housing and configured to connect to a motion controller, the connector housing receiving one or more of: a body connector configured to receive a proximal portion of a body a body configured to fit within a lumen of the female reproductive system, the body connector slidable relative to the connector housing at a fixed orientation, and a lead screw for advancing the body connector; and/or an inner body connector configured to receive a proximal portion of an inner body slidably received in a lumen of a body configured to fit within a lumen of the female reproductive system, the inner body connector slidable relative to the connector housing, optionally at a fixed orientation, and a lead screw for advancing the inner body connector; and/or a plunger connector configured to receive a proximal portion of a plunger slidably received by an inner body slidably received in a lumen of a body configured to fit within a lumen of the female reproductive system, the plunger connector slidable relative to the connector housing, optionally at a fixed orientation, and a lead screw for advancing the plunger connector.

A proximal end of one or more of the lead screws for advancing the body connector, inner body connector or plunger connector may comprise teeth for rotationally locking the one or more lead screws to corresponding lead screw drivers of a motion controller.

The connector may be configured to releasably connect to the motion controller, optionally at a fixed orientation.

The connector (e.g. body connector) may comprise an electrical terminal configured to connect to an electrical terminal of the motion controller. The connector (e.g. body connector) may comprise an optical terminal configured to form a face seal with an optical terminal of the motion controller.

A motion controller configured to connect to the connector disclosed above and to drive one or more of the lead screws.

The motion controller may comprise one or more lead screw drivers, the one or more lead screw drivers comprises teeth for rotationally locking to the corresponding lead screw. The lead screw drivers may be distally biased towards the connector.

The motion controller may be configured to releasably connect to the connector, optionally at a fixed orientation.

The motion controller may comprise an electrical terminal configured to connect to an electrical terminal of the connector, wherein the electrical terminal of the motion controller is biased towards the electrical terminal of the connector to maintain electrical contact.

The motion controller may comprise an optical terminal configured to form a face seal with an optical terminal of the controller, wherein the optical terminal of the motion controller is biased towards the optical terminal of the connector to maintain the face seal.

The following clauses also form part of the present disclosure:

1. An apparatus suitable for delivering a fertilized egg or embryo into a maternal uterine endometrium in humans or any other mammalian species, comprising a body configured to fit within a lumen of the female reproductive system, the body comprising:
   a lumen extending from a proximal end of the body to a distal portion of the body and having a distal opening at the distal portion of the body, the lumen configured to slidably receive an inner body having a distal end suitable for penetrating the endometrial epithelium;
   the apparatus further comprising:
   a measurement assembly comprising a measurement portion disposed at the distal portion of the body, the measurement assembly configured to measure whether the apparatus is in a first state indicating that a distance between the distal portion and the endometrial epithelium is greater than a predetermined distance, or a second state indicating that a distance between the distal portion and the endometrial epithelium is equal to or less than a predetermined distance;
   an indicating device coupled to the measurement assembly and configured to indicate that the measurement assembly is in the first state or the second state; and
   a first actuator operable to advance the inner body out from the distal opening by at least the predetermined distance, and a second actuator operable to expel a fertilized egg from the inner body.
2. The apparatus of clause 1, wherein the measurement assembly comprises:
   one or more light sources proximal the distal opening, each configured to emit light from the distal portion of the body; and
   one or more converging lenses configured to focus the one or more light sources at a focal point away from the distal opening; and
   an imaging device having a field of view including the focal point;
   wherein when the emitted light is incident on the endometrial epithelium at the focal point, the distal opening is at the predetermined distance away from the endometrial epithelium;
   optionally wherein the indicating device comprises a display of the imaging device.
3. The apparatus of clause 2, wherein the imaging device comprises a camera, or a fiberscope.
4. The apparatus of clause 2 or 3, further comprising a secondary light source configured to emit unfocussed light onto the endometrial epithelium from the distal portion of the body.

5. The apparatus of any of clauses 2 to 4, wherein the one or more light sources comprise two or more separated light sources, such that the light sources converge at the focal point, wherein when the incident light on the endometrial epithelium from the light sources converge, the distal opening is within the predetermined proximity; preferably wherein the one or more light sources comprise three or more separated light sources.
6. The apparatus of clause 1, wherein the measurement assembly comprises an optical coherence tomography (OCT) scanning probe comprising an OCT fiber bundle terminating proximal to the distal opening, the OCT scanning probe configured to calculate the distance of the distal opening to a portion of the endometrial epithelium.
7. The apparatus of clause 1, wherein the measurement assembly comprises a camera proximal the distal opening and configured to view a portion of the endometrial epithelium, wherein the depth of field of the camera has a predetermined value, such that when the image is in focus, the distal opening is at the predetermined distance to the endometrial epithelium; optionally wherein the indicating device comprises a display for displaying an image captured by the camera.
8. The apparatus of clause 1, wherein the measurement assembly comprises a confocal probe.
9. The apparatus of clause 1, wherein the measurement assembly comprises laser probe comprising an optical fiber terminating proximal to the distal opening, the laser probe configured to measure the time of flight of laser radiation transmitted to the endometrial epithelium and reflected back to the laser probe through the optical fiber.
10. The apparatus of clause 1, wherein the measurement portion comprises a light source having a fixed aperture configured to illuminate a shape on the endometrial epithelium, and an imaging device having a field of view including the illuminated region; wherein the viewed shape being bigger than a predetermined size indicates the first state, and the viewed shape matching or being smaller than the predetermined size indicates the second state;
    optionally wherein the indicating device comprises a display coupled to the imaging device, the display comprising a view of the illuminated endometrial epithelium and a comparison overlay, wherein the comparison overlay is sized and shaped such that the viewed shape being bigger than the comparison overlay indicates the first state, and the viewed shape matching or being smaller than the comparison overlay indicates the second state.
11. The apparatus of clause 1, wherein the measurement portion comprises a light source and a stereo camera configured to image the endometrial epithelium, the measurement assembly configured to calculate a distance of the distal opening to the endometrial epithelium.
12. The apparatus of clause 1, wherein the measurement portion comprises a light source configured to illuminate the endometrial epithelium, a rigid protrusion positioned to cast a shadow onto the endometrial epithelium, and an imaging device having a field of view including the shadow; wherein the protrusion is positioned such that when an edge of the viewed shadow crosses a predetermined location in the field of view, the measurement assembly transitions from the first state to the second state; optionally wherein the indicating device is a display coupled to the imaging device and displaying a view of the imaging device, the display further comprising a comparison overlay, wherein the comparison overlay is positioned such that when an edge of the viewed shadow crosses the comparison overlay as the body is advanced, the measurement assembly transitions from the first state to the second state.
13. The apparatus of clause 1, wherein the measurement assembly comprises an ultrasound probe comprising an emitter and receiver proximate the distal opening configured to emit sound waves towards the endometrial epithelium, the measurement assembly configured to calculate the distance of the distal opening to the endometrial epithelium.
14. The apparatus of clause 1, wherein the measurement portion comprises a light source configured to illuminate a resiliently deformable protrusion, the protrusion configured to extend towards the endometrial epithelium, and an imaging device having a field of view of the protrusion; wherein the protrusion being undeformed indicates the first state and the protrusion being deformed indicates the second state; optionally wherein the indicating device comprises a display coupled to the imaging device.
15. The apparatus of clause 1, wherein the measurement assembly comprises a pressure sensor located on the part of the distal portion which is configured to impact the endometrial epithelium first as the body is advanced; wherein the predetermined distance is zero and the first state is indicated by a pressure measurement below a threshold value, and the second state is indicated by a pressure measurement above the threshold value.
16. The apparatus of any preceding clause, further comprising a steering mechanism configured to steer a distal portion of the body and a third actuator for operating the steering mechanism.
17. The apparatus of clause 16, wherein the steering mechanism comprises:
    a plurality of connected rings forming a tube wall configured to at least partially surround a portion of the body; and
    at least one cable extending longitudinally along the tube wall and attached to a distal end of the tube wall;
    wherein the third actuator is operable to contract and extend at least one cable to steer the distal portion of the body;
    preferably wherein the steering mechanism comprises a plurality of said cables located at different circumferential positions about the tube wall.
18. The apparatus of clause 17, wherein the third actuator comprises:
    an inner element;
    an outer shell housing the inner element, each of the at least one cable being fixedly connected to the outer shell at a proximal portion;
    the inner element being fixedly connected to the tube wall;
    the outer shell being rotatable relative to the inner element; and
    optionally, a handle fixed to the inner element through the outer shell.
19. The apparatus of clause 18, wherein the inner element comprises one or more components biased to abut the outer shell.

20. The apparatus of any of clauses 16 to 19, wherein the body is slidable relative to the steering mechanism and third actuator.
21. The apparatus of any preceding clause, further comprising a balloon catheter, the balloon catheter comprising:
    an outer tubular body; and
    an evertable tube slidably received in the outer tubular body and configured to receive the steering mechanism or body; wherein the balloon catheter is configured to contain a fluid between the outer tubular body and the evertable tube; and
    when the steering mechanism or body is advanced, the evertable tube everts.
22. The apparatus of clause 21, wherein the balloon catheter comprises a fluid port for filling the balloon catheter with fluid.
23. The apparatus of clause 22, wherein the fluid port is fluidically connected to a reservoir of fluid.
24. The apparatus of clause 23, wherein the reservoir is formed by a piston housing and a piston, and a biasing mechanism configured to bias the piston distally to pressurise the fluid in the reservoir.
25. The apparatus of clause 24, further comprising a releasable locking mechanism for locking the piston in a proximal position.
26. The apparatus of clause 23 or 24, wherein the piston housing and piston are configured to slidably receive the steering mechanism or body.
27. The apparatus of any of clauses 23 to 26, wherein the maximum volume of the reservoir is less than an overfilling volume of the balloon catheter.
28. The apparatus of any of clauses 21 to 27, wherein the steering mechanism or body is fixed to the tubular balloon such that the steering mechanism or body is advanceable to a maximum position.
29. The apparatus of any preceding clause, further comprising a plunger slidably received by the inner body, wherein the second actuator is operable to expel a fertilized egg from the inner body by sliding the plunger distally relative to the inner body; optionally wherein the second actuator comprises a lead screw for advancing the plunger.
30. The apparatus of clause 29, wherein the first actuator is configured to retract the inner body as the plunger is slid distally relative to the inner body.
31. The apparatus of any preceding clause, further comprising a motion controller configured to connect to a proximal portion of the body, the controller configured to actuate one or more of the first actuator, second actuator, and/or a fourth actuator for advancing the body relative to the motion controller.
32. The apparatus of clause 31, wherein one or more of the first, second and fourth actuators comprises a lead screw, and the motion controller is configured to actuate one or more of the lead screws.
33. The apparatus of clause 32, further comprising a connector having a connector housing and configured to connect to the motion controller, the connector housing receiving one or more of:
    a body connector fixedly receiving a proximal portion of the body, the body connector slidable relative to the connector housing at a fixed orientation, wherein the fourth actuator comprises a lead screw for advancing the body connector; and/or
    an inner body connector fixedly receiving a proximal portion of the inner body, the inner body connector slidable relative to the connector housing, optionally at a fixed orientation, wherein the first actuator comprises a lead screw for advancing the inner body connector; and/or
    a plunger connector fixedly receiving a proximal portion of a plunger slidably received by the inner body, the plunger connector slidable relative to the connector housing, optionally at a fixed orientation, wherein the second actuator comprises a lead screw for advancing the plunger connector.
34. The apparatus of clause 33 wherein a proximal end of one or more of the lead screws for advancing the body connector, inner body connector or plunger connector comprises teeth for rotationally locking the one or more lead screws to corresponding lead screw drivers of the motion controller, optionally wherein the lead screw drivers are distally biased towards the connector.
35. The apparatus of clause 33 or 34, wherein the connector is configured to releasably connect to the motion controller, optionally at a fixed orientation.
36. The apparatus of any of clauses 32 to 35 wherein the measurement portion is electrically connected to a first electrical terminal of the connector, and the motion controller comprises a corresponding second electrical terminal biased towards the first electrical terminal to maintain contact with the first electrical terminal; and/or wherein the measurement portion is optically connected to a first optical terminal of the connector, and the motion controller comprises a corresponding second optical terminal configured to form a face seal with the first optical terminal and biased towards the first optical terminal to maintain the face seal with the first optical terminal.
37. The apparatus of any preceding clause, wherein the measurement assembly comprises an electronic output indicating the measurement of the measurement portion, and the indicating device is configured to analyse the electronic output to determine whether the measurement assembly is in the first state or the second state.
38. The apparatus of clause 37, wherein the indication is configured to be provided to an electronic controller configured to control one or more actuators.
39. The apparatus of any preceding clause, wherein one or more of the actuators are electronically controlled.
40. A computer program product configured to control the apparatus of clause 39, comprising instructions which, when the program is executed by a computer, cause the computer to carry out the following steps:
    receive an instruction to actuate one or more electronically controlled actuators; and actuate the one or more electronically controlled actuators.

All of the above are fully within the scope of the present disclosure, and are considered to form the basis for alternative embodiments in which one or more combinations of the above described features are applied, without limitation to the specific combination disclosed above.

In light of this, there will be many alternatives which implement the teaching of the present disclosure. It is expected that one skilled in the art will be able to modify and adapt the above disclosure to suit its own circumstances and requirements within the scope of the present disclosure, while retaining some or all technical effects of the same, either disclosed or derivable from the above, in light of his common general knowledge in this art. All such equivalents, modifications or adaptations fall within the scope of the present disclosure.

The invention claimed is:

1. An apparatus suitable for delivering a fertilized egg or embryo into a maternal uterine endometrium in a mammalian species, the apparatus comprising:
- a body configured to fit within a lumen of the female reproductive system, the body comprising:
  - a lumen extending from a proximal end of the body to a distal portion of the body and having a distal opening at the distal portion of the body, the lumen configured to slidably receive an inner body having a distal end suitable for penetrating an endometrial epithelium;
- a first actuator operable to advance the inner body out from the distal opening of the body;
- a second actuator operable to expel a fertilized egg from the inner body;
- a measurement assembly configured to measure whether the apparatus is in a first state indicating that a distance between the distal end of the inner body and the endometrial epithelium is greater than a predetermined distance in a direction that the inner body is advanced from the distal opening, or a second state indicating that the distance between the distal end of the inner body and the endometrial epithelium is equal to or less than the predetermined distance; and
- an indicating device coupled to the measurement assembly and configured to indicate that the apparatus is in the first state or the second state.

2. The apparatus of claim 1, wherein the measurement assembly is configured to:
- make electrical contact with a distal portion of the inner body which is electrically conductive; and
- provide an indication of capacitance, wherein the first state is indicated by a capacitance measurement below a threshold value, and the second state is indicated by a capacitance measurement above the threshold value.

3. The apparatus of claim 2, wherein the predetermined distance is zero.

4. The apparatus of claim 1, further comprising:
- an imaging device having a field of view including a focal point away from the distal opening.

5. The apparatus of claim 1, further comprising:
- a steering mechanism configured to steer the distal portion of the body; and
- a third actuator for operating the steering mechanism.

6. The apparatus of claim 5, further comprising:
- a balloon catheter comprising:
  - an outer tubular body, and
  - an evertable tube slidably received in the outer tubular body and configured to receive the steering mechanism or the body,
- wherein
- the balloon catheter is configured to contain a fluid between the outer tubular body and the evertable tube; and
- when the steering mechanism or the body is advanced, the evertable tube everts.

7. The apparatus of claim 1, further comprising:
- a plunger slidably received by the inner body, wherein;
- the second actuator is operable to expel a fertilized egg from the inner body by sliding the plunger in a distal direction relative to the inner body;
- the second actuator comprises a lead screw for advancing the plunger; and/or
- the first actuator is configured to retract the inner body as the plunger is slid distally relative to the inner body.

8. The apparatus of claim 1, further comprising:
- a motion controller configured to connect to a proximal portion of the body, the motion controller comprising one or more lead screws configured to advance/retract the body and/or to advance/retract and/or rotate an outer catheter housing the body.

9. The apparatus of claim 8, wherein the motion controller comprises one or more actuation mechanisms configured to actuate one or more of the lead screws.

10. The apparatus of claim 1, further comprising:
- a motion controller configured to connect to a proximal portion of the body, wherein the motion controller is configured to actuate one or more of the first actuator, second actuator, and/or a fourth actuator for advancing the body relative to the motion controller.

11. The apparatus of claim 10, wherein:
- one or more of the first, second and fourth actuators comprises at least one lead screw; and
- the motion controller is configured to actuate the at least one lead screw.

12. The apparatus of claim 1, wherein:
- the measurement assembly comprises an electronic output; and
- the indicating device is configured to analyze the electronic output to determine whether the apparatus is in the first state or the second state.

13. The apparatus of claim 12, wherein the indicating device is further configured to provide an indication to an electronic controller configured to control at least one of the first actuator and the second actuator.

14. The apparatus of claim 1, wherein at least one of the first actuator and the second actuator is electronically controlled.

15. A computer program product configured to control the apparatus of claim 14, the computer program product comprising instructions which, when executed by a computer, cause a computer to:
- receive an instruction to actuate one or more electronically controlled actuators; and
- actuate the at least one of the first actuator and the second actuator.

16. An apparatus suitable for delivering a fertilized egg or embryo into a maternal uterine endometrium in a mammalian species, the apparatus comprising:
- a body configured to fit within a lumen of the female reproductive system, the body comprising:
  - a lumen extending from a proximal end of the body to a distal portion of the body and having a distal opening at the distal portion of the body, the lumen configured to slidably receive an inner body having a distal end suitable for penetrating an endometrial epithelium;
- a first actuator operable to advance the inner body out from the distal opening of the body;
- a second actuator operable to expel a fertilized egg from the inner body;
- a measurement assembly comprising a measurement portion disposed at the distal portion of the body, the measurement assembly being configured to measure whether the apparatus is in a first state indicating that a distance between the distal portion of the body and the endometrial epithelium is greater than a predetermined distal portion distance in a direction that the inner body is advanced from the distal opening, or a second state indicating that the distance between the distal portion of the body and the endometrial epithelium is equal to or less than the predetermined distal portion distance; and an indicating device coupled to the measurement assembly and configured to indicate that the measurement assembly is in the first state or the second state;

wherein the first actuator is operable to advance the inner body out from the distal opening by at least the predetermined distance.

17. The apparatus of claim 16, wherein the measurement assembly further comprises:

one or more light sources proximal to the distal opening, each light source configured to emit light from the distal portion of the body;

one or more converging lenses configured to focus the one or more light sources at a focal point away from the distal opening; and an imaging device having a field of view including the focal point, wherein, when the light emitted from the distal portion of the body is incident on the endometrial epithelium at the focal point, the distal opening is at the predetermined distance away from the endometrial epithelium.

18. The apparatus of claim 17, wherein;

the one or more light sources comprise two or more separated light sources, such that the light sources converge at the focal point; and, when incident light on the endometrial epithelium from the two or more separated light sources converge, the distal opening is within the predetermined distance.

19. The apparatus of claim 16, wherein:

the measurement assembly further comprises a capacitive sensor located on part of the distal portion of the body which is configured to impact the endometrial epithelium first as the body is advanced, and the measurement assembly is configured to provide an indication of capacitance as the distance between the distal portion of the body and the endometrial epithelium changes; or the measurement assembly comprises an electrically conductive element located on the part of the distal portion of the body which is configured to impact the endometrial epithelium first as the body is advanced, and the measurement assembly is configured to provide an indication of capacitance as the distance between the distal portion of the body and the endometrial epithelium changes.

20. The apparatus of claim 19, wherein:

the predetermined distance is zero;

the first state is indicated by a capacitance measurement below a threshold value; and the second state is indicated by a capacitance measurement above the threshold value.

21. The apparatus of claim 16, wherein the measurement assembly is further configured to measure whether the apparatus is in a third state indicating that a distance between the distal end of the inner body and the endometrial epithelium is greater than a predetermined distal end distance, or a fourth state indicating that the distance between the distal end of the inner body and the endometrial epithelium is equal to or less than a predetermined distal end distance; and the indicating device is further configured to indicate that the apparatus is in the third state or the fourth state.

22. The apparatus of claim 21, wherein the measurement assembly is configured to make electrical contact with a distal portion of the inner body which is electrically conductive, and to provide an indication of capacitance;

the third state is indicated by a capacitance measurement below a threshold value;

the fourth state is indicated by a capacitance measurement above the threshold value; and the predetermined distal end distance is zero.

* * * * *